United States Patent [19]
Reiter et al.

[11] Patent Number: 6,093,800
[45] Date of Patent: Jul. 25, 2000

[54] E25A PROTEIN, METHODS FOR PRODUCTION AND USE THEREOF

[75] Inventors: Robert E. Reiter, Los Angeles; Owen N. Witte, Sherman Oaks; Charles L. Sawyers, Los Angeles, all of Calif.

[73] Assignee: The Regents of the University of California, Oakland, Calif.

[21] Appl. No.: 08/924,570

[22] Filed: Sep. 5, 1997

Related U.S. Application Data

[60] Provisional application No. 06/025,569, Sep. 6, 1996.

[51] Int. Cl.$^7$ ........................................................ C07K 5/00
[52] U.S. Cl. ............................................................. 530/350
[58] Field of Search ....................................... 530/350, 395

[56] References Cited

FOREIGN PATENT DOCUMENTS

94/09820  5/1994  WIPO .

OTHER PUBLICATIONS

Hillier, L., et al., "The WashU–Merck EST project, AC W37917," *EMBL Database*, Heidelberg, XP002058366. May 17, 1996.

Hillier, L., et al., "The WashU–Merck EST project AC N32815," *EMBL Database*, Heidelberg, XP002058367. Jan 13, 1996.

Deleersnijder, W., et al., "Isolation of markers for chondro–osteogenic differentiation using cDNA library subtraction," *The Journal of Biochemical Chemistry*, 271(32):19475–19482, XP002058368. Aug. 9, 1996.

Reiter, R., et al., "Representational difference analysis of human androgen independent prostate cancer," *Proceedings of the American Association for Cancer Research*, 37:246–247, XP002058557. Mar. 1996.

Raffo, A., et al., "Overexpression of bcl–2 protects prostate cancer cells form apoptosis in vitro and confers resistance to androgen depletion in vivo," *Cancer Research*, 55(19):4438–4445. XP002058467. Oct. 1, 1995.

Rinker–Schaeffer, C., et al., "Molecular and cellular changes associated with the acquisition of metastatic ability by prostatic cancer cells," *The Prostate*, 25(5):249–265, XP002058468. 1994.

Reiter, R., et al., "Two genes upregulated in androgen–independent prostate cancer are also selectively expressed in the basal cells of normal prostate epithelium," *Journal of Urology, Supplement*, 157(4):269, XP002058558. Apr. 4, 1997.

*Primary Examiner*—Sheela Huff
*Attorney, Agent, or Firm*—Mandel & Adriano

[57] ABSTRACT

The invention provides a human E25a protein which is upregulated in cancerous cells, including those of hormone refractory prostate cancer, colon cancer, breast cancer or other cancers of epithelial origin. The invention also provides nucleic acid molecules encoding E25a protein, nucleic acid probes which hybridize with nucleic acid molecules encoding E25a protein, and antibodies which bind E25a protein. E25a protein and its related molecules can be useful as diagnostic markers of cancer, including hormone refractory prostate cancer, and as specific therapeutic targets in this disease. The invention also provides methods for diagnosing cancer, including hormone refractory prostate cancer.

1 Claim, 15 Drawing Sheets

FIG. 1

Human E25 nucleotide sequence and peptide

```
gatctcctcttgcagtctgcagcccaggacgctgattccagcagcgccttaccgcgcagccgaagattcact
atg gtg aaa atc gcc ttc aat acc cct acc gcc gtg caa aag gag gag gcg cgg caa gac
 M   V   K   I   A   F   N   T   P   T   A   V   Q   K   E   E   A   R   Q   D
gtg gag gcc ctc ctg agc cgc acg gtc aga act cag ata ctg acc ggc aag gag ctc cga
 V   E   A   L   L   S   R   T   V   R   T   Q   I   L   T   G   K   E   L   R
gtt gcc acc cag gaa aaa gag ggc tcc tct ggg aga tgt atg ctt act ctc tta ggc ctt
 V   A   T   Q   E   K   E   G   S   S   G   R   C   M   L   T   L   L   G   L
tca ttc atc ttg aca gga ctt att gtt ggt gga gcc tgc att tac aag tac ttc atg ccc
 S   F   I   L   T   G   L   I   V   G   G   A   C   I   Y   K   Y   F   M   P
aag agc acc att tac cgt gga gag atg tgc ttt ttt gat tct gag gat cct gca aat tcc
 K   S   T   I   Y   R   G   E   M   C   F   F   D   S   E   D   P   A   N   S
ctt cgt gga gga gag cct aac ttc ctg cct gtg act gag gag gct gac att cgt gag gat
 L   R   G   G   E   P   N   F   L   P   V   T   E   E   A   D   I   R   E   D
gac aac att gca atc att gat gtg cct gtc ccc agt ttc tct gat agt gac cct gca gca
 D   N   I   A   I   I   D   V   P   V   P   S   F   S   D   S   D   P   A   A
att att cat gac ttt gaa aag gga atg act gct tac ctg gac ttg ttg ctg ggg aac tgc
 I   I   H   D   F   E   K   G   M   T   A   Y   L   D   L   L   L   G   N   C
tat ctg atg ccc ctc aat act tct att gtt atg cct cca aaa aat ctg gta gag ctc ttt
 Y   L   M   P   L   N   T   S   I   V   M   P   P   K   N   L   V   E   L   F
ggc aaa ctg gcg agt ggc aga tat ctg cct gaa act tat gtg gtt cga gaa gac cta gtt
 G   K   L   A   S   G   R   Y   L   P   E   T   Y   V   V   R   E   D   L   V
gct gtg gag gaa att cgt gat gtt agt aac ctt ggc atc ttt att tac caa ctt tgc
 A   V   E   E   I   R   D   V   S   N   L   G   I   F   I   Y   Q   L   C
aat aac aga aag tcc ttg tcc ctt cgt cgc aga gac ctc ttg ctg ggt ttc aac aaa cgt gcc
 N   N   R   K   S   L   S   L   R   R   R   D   L   L   L   G   F   N   K   R   A
att gat aaa tgc tgg aag att aga cac ttc ccc aac gaa ttt att gtt gag acc aag atc
 I   D   K   C   W   K   I   R   H   F   P   N   E   F   I   V   E   T   K   I
tgt caa gag taa
 C   Q   E   stop
```

Bold and underlined = putative transmembrane domain

1. LAPC-4 Androgen Responsive
2. LAPC-4 Androgen Independent
3. LNCaP
4. LNCaP Androgen Independent
5. Stage B adenocarcinoma
6. Normal
7. BPH In vitro transcription-translation of a full length cDNA corresponding to RDA clones +7 and +18. The encoded peptide, R1, is ~40KD and encodes a putative type II membrane protein.

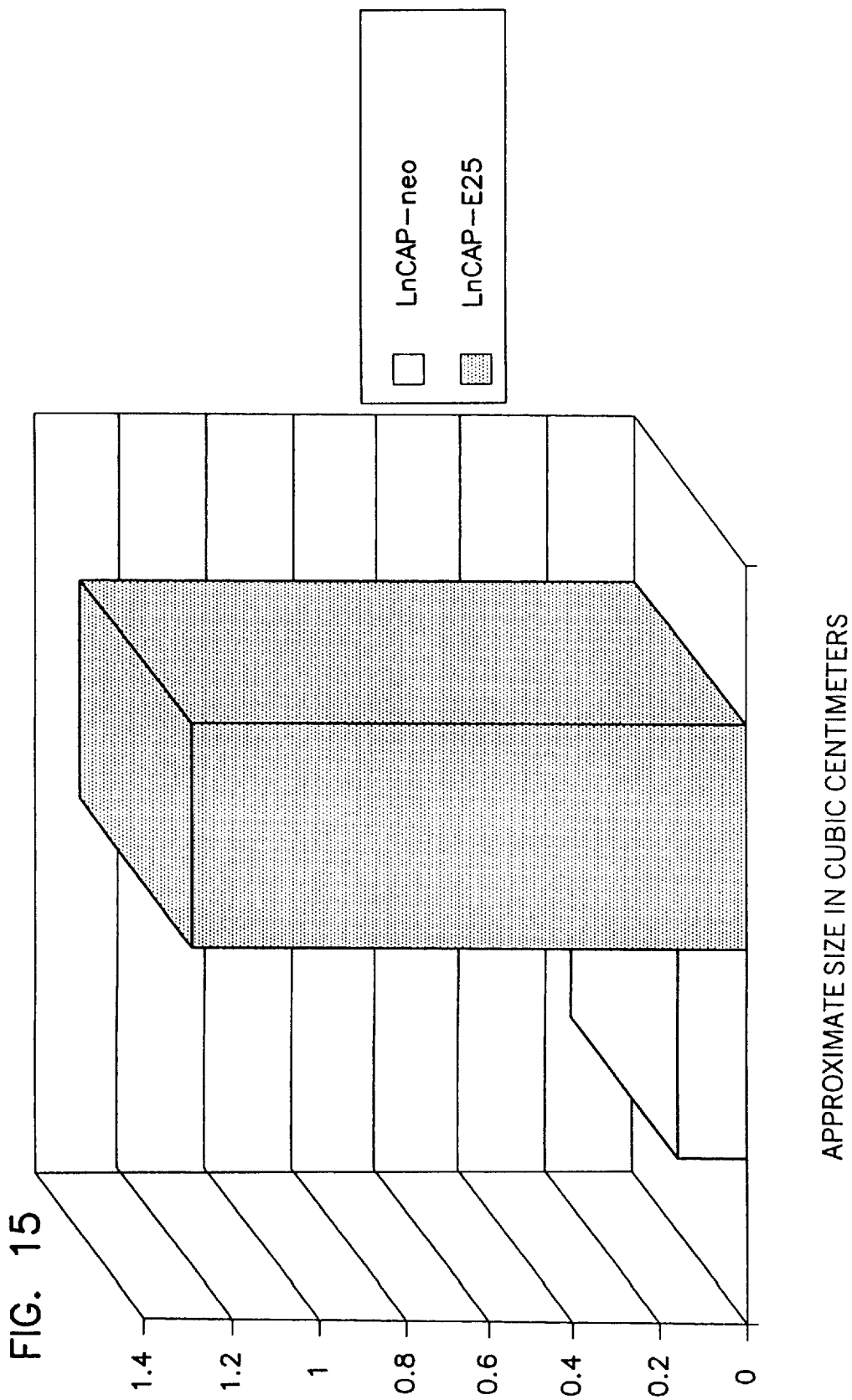

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 864 base pairs
        (B) TYPE: nucleic acid
        (C) STRANDEDNESS: unknown
        (D) TOPOLOGY: unknown (ii) MOLECULE TYPE: Other (ix) FEATURE:

(xi) SEQUENCE DESCRIPTION: SEQ ID NO:1:

```
GATCTCCTCT TGCAGTCTGC AGCCCAGGAC GCTGATTCCA GCAGCGCCTT ACCGCGCAGC      60

CGAAGATTCA CTATGGTGAA AATCGCCTTC AATCAACCTA CCCCTACCGC CGTGCAAAAG     120

GAGGAGGCGC GGCAAGACGT GGAGGCCCTC CTGAGCCGCA CGGTCAGAAC TCAGATACTG     180

ACCGGCAAGG AGCTCCGAGT TGCCACCCAG GAAAAAGAGG GCTCCTCTGG GAGATGTATG     240

CTTACTCTCT TAGGCCTTTC ATTCATCTTG ACAGGACTTA TTGTTGGTGG AGCCTGCATT     300

TACAAGTACT TCATGCCCAA GAGCACCATT TACCGTGGAG AGATGTGCTT TTTTGATTCT     360

GAGGATCCTG CAAATTCCCT TCGTGGAGGA GAGCCTAACT TCCTGCCTGT GACTGAGGAG     420

GCTGACATTC GTGAGGATGA CAACATTGCA ATCATTGATG TGCCTGTCCC CAGTTTCTCT     480

GATAGTGACC CTGCAGCAAT TATTCATGAC TTTGAAAAGG GAATGACTGC TTACCTGGAC     540

TTGTTGCTGG GGAACTGCTA TCTGATGCCC CTCAATACTT CTATTGTTAT GCCTCCAAAA     600

AATCTGGTAG AGCTCTTTGG CAAACTGGCG AGTGGCAGAT ATCTGCCTCC AAAAAATCTG     660

GTAGAGCTCT TTGCTGTGGA GGAAATTCGT GATGTTAGTA ACCTTGGCAT CTTTATTTAC     720

CAACTTTGCA ATAACAGAAA GTCCTTGTCC CTTCGTCGCA GAGACCTCTT GCTGGGTTTC     780
```

```
AACAAACGTG CCATTGATAA ATGCTGGAAG ATTAGACACT TCCCCAACGA ATTTATTGTT     840

GAGACCAAGA TCTGTCAAGA GTAA                                            864
```

(2) INFORMATION FOR SEQ ID NO:2:

(i) SEQUENCE CHARACTERISTICS:
        (A) LENGTH: 264 amino acids
        (B) TYPE: amino acid
        (C) STRANDEDNESS: unknown
        (D) TOPOLOGY: unknown (ii) MOLECULE TYPE: protein (v) FRAGMENT TYPE: internal (xi) SEQUENCE DESCRIPTION: SEQ ID NO:2:

```
Met Val Lys Ile Ala Lys Asn Thr Pro Thr Ala Val Gln Lys Glu Glu
1               5                  10                  15

Ala Arg Gln Asp Val Glu Ala Leu Leu Ser Arg Thr Val Arg Thr Gln
            20                  25                  30

Ile Leu Thr Gly Lys Glu Leu Arg Val Ala Thr Glu Lys Glu Gly Ser
        35                  40                  45

Ser Gly Arg Cys Met Leu Thr Leu Leu Gly Leu Ser Phe Ile Leu Thr
    50                  55                  60

Gly Leu Ile Val Gly Gly Ala Cys Ile Tyr Lys Tyr Phe Met Pro Lys
65                  70                  75                  80

Ser Thr Ile Tyr Arg Gly Glu Met Cys Phe Phe Asp Ser Glu Asp Pro
                85                  90                  95

Ala Asn Ser Leu Arg Gly Gly Glu Pro Asn Phe Leu Pro Val Thr Phe
            100                 105                 110

Glu Ala Asp Ile Arg Glu Asp Asp Asn Ile Ala Ile Ile Asp Val Pro
        115                 120                 125

Val Pro Val Pro Ser Phe Ser Asp Ser Asp Pro Ala Ala Ile Ile His
    130                 135                 140

Asp Phe Glu Lys Gly Met Thr Ala Tyr Leu Asp Leu Leu Leu Gly Asn
145                 150                 155                 160

Cys Tyr Leu Met Pro Leu Asn Thr Ser Ile Val Met Pro Pro Lys Asn
                165                 170                 175

Leu Val Glu Leu Pro Gly Lys Leu Ala Ser Gly Arg Tyr Leu Pro Gln
            180                 185                 190

Thr Tyr Val Val Arg Lys Asp Leu Val Ala Val Glu Ile Arg Asp
        195                 200                 205

Val Ser Asn Leu Gly Ile Phe Ile Tyr Gln Leu Cys Asn Asn Arg Lys
    210                 215                 220

Ser Leu Ser Leu Arg Arg Arg Asp Leu Leu Leu Gly Phe Asn Lys Arg
225                 230                 235                 240

Ala Ile Asp Lys Cys Trp Lys Ile Arg His Phe Pro Asn Glu Phe Ile
                245                 250                 255

Val Glu Thr Lys Ile Cys Gln Glu
            260
```

E25A PROTEIN, METHODS FOR PRODUCTION AND USE THEREOF

This application is based on a provisional application, U.S. Ser. No. 06/025,569, filed Sep. 6, 1996, the contents of which are hereby incorporated by reference into this application.

Throughout this application, various publications are referenced within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Prostate cancer is currently the most common type of cancer in American men and the second leading cause of cancer related death in this population. In its advanced stages, prostate cancer metastasizes preferentially to bone, where it forms osteoblastic lesions. After initial treatment with androgen ablation therapy, most metastatic prostate cancers become hormone-refractory and lethal. The major cause of morbidity and mortality from prostate cancer is advanced stage, androgen independent disease.

There is currently no effective therapy for hormone refractory prostate cancer and there is currently no marker specific for hormone refractory prostate cancer. In addition to an urgent need for new therapies, there is also a need for diagnostic tests of hormone refractory-prostate cancer. Such tests would indicate which patients have hormone refractory cancer cells at diagnosis and where they are located. This information would have a profound impact on initial therapy. In addition, markers of hormone independent prostate cancer could be used to detect recurrent disease and could be used as therapeutic targets.

Despite recent advances in the diagnosis and treatment of localized prostate cancer, little progress has been made in the fight against advanced disease. Virtually all patients treated with hormone ablation therapy will go on to develop androgen independent recurrences, for which there currently is no therapy. Knowledge of the specific molecular events underlying the progression of prostate cancer to androgen independence is limited.

An understanding of the mechanism of androgen independent growth would provide the framework for the development of rational therapies. The development of specific markers of androgen independent growth would lead to the early identification of patients at risk to fail surgical or hormonal therapy and to the selection of patients for alternative therapies. A number of hypotheses have been advanced to explain the biological basis of androgen independence.

One hypothesis is that androgen independence arises through alterations in the androgen receptor. These alterations include overexpression of the androgen receptor, amplification, or mutation (Kokontis et al., 1994; Visakorpi et al., 1995). Taplin et al. recently demonstrated androgen receptor mutations in 50% of patients with hormone refractory disease (Taplin et al., 1995). Mutated receptors have been demonstrated to respond to ligands other than testosterone, including estrogen, insulin growth factor, the androgen antagonist flutamide, and keratinocyte growth factor (Culig et al., 1994; Scher and Kelly, 1993).

Although androgen receptor mutations may contribute to androgen independence, evidence supports the existence of alternative mechanisms. The prostate cancer cell line LNCaP maintains its androgen dependence despite an androgen receptor mutation that renders it sensitive to estrogen (Culig et al., 1994; Veldsholte et al., 1990). Similarly, in androgen receptor negative, androgen independent cell lines such as PC3, introduction of functional androgen receptor does not restore androgen sensitivity, suggesting that androgen receptor is not all that is necessary for androgen sensitivity (Krongrad et al., 1991; Yuan et al., 1993).

Other mechanisms of androgen independence have been proposed. BcL-2 overexpression correlates with hormone resistance, and hyperexpression of bcl-2 in LNCaP prostate cancer cells can confer androgen independence in vivo (McDonnell et al., 1992; Raffo et al., 1995). p53 mutation, c-myc overexpression and protein kinase C activation have also been associated with advanced prostate cancer and hormone resistance in some patients and cell lines (Bookstein et al., 1993; Kokontis et al., 1994; Krongrad and Bai, 1994; Raffo et al., 1995).

The mechanisms by which bcl-2, c-myc and other genes mediate androgen resistance are not known. One hypothesis is that androgen independence represents an arrested stage of stem cell development. Supporting this hypothesis is the finding that c-met and bcl-2 expression is restricted to the basal epithelium of normal prostate, which contains the androgen independent prostatic stem cell population (Bonkhoff and Remberger, 1996; Bonkhoff et al., 1994; Pisters et al., 1995). A gene disclosed herein, E25a, also is expressed in basal epithelium of normal prostate, supporting this hypothesis. Androgen independence, therefore, may result from upregulation of stem cell genes that promote immortalization and/or self renewal.

SUMMARY OF THE INVENTION

The invention provides a cell-surface protein designated E25a which is upregulated in cancerous cells, including those of hormone refractory prostate cancer, colon cancer, breast cancer or other cancers of epithelial origin. The invention also provides related molecules such as nucleic acid molecules encoding E25a protein, nucleic acid probes which hybridize with nucleic acid molecules encoding E25a protein, and antibodies which bind E25a protein. The E25a nucleic acid molecule and its related molecules can be useful as diagnostic markers of cancer, including hormone refractory prostate cancer, and as specific therapeutic targets in this disease. The invention also provides methods for diagnosing cancer, including hormone refractory prostate cancer. In addition, the invention provides methods for inhibiting expression of E25a nucleic acid molecule, for inhibiting proliferation of cancer cells and for treating cancer.

BRIEF DESCRIPTION OF THE FIGURES

FIG. 1 shows the nucleic acid sequence and amino acid sequence of human E25a. The bold and underlined portion indicates the transmembrane domain (amino acids 52–76).

FIG. 2A shows PCR analysis using primers specific for the human β-globin gene, performed for 30 cycles with 100 ng of genomic DNA isolated from the LAPC xenografts. One-tenth of each reaction was analyzed by electrophoresis through agarose gels and visualized by staining with ethidium bromide. Each sample shown in the figure was obtained from late passage xenografts. The LAPC-5 sample was obtained at passage 4 when the human tumor was overgrown by a tumor of murine origin (see text and Table 1). The two LAPC-4 samples were obtained from androgen dependent (AD) and androgen independent (AI) sublines. NIH3T3 cells are murine fibroblasts and serve as a negative control.

FIG. 2B shows RT-PCR analysis, performed on 100 ng of total RNA using primers specific for human PSA (top panel). The same RNA samples were analyzed using primers which recognize human or murine β-actin (bottom panel) to confirm equivalent loading. A dilution series of human prostate cancer LNCaP cells into murine NIH3T3 cells is shown on the left side of the figure with the percentage of LNCaP cells varied from 100 to 0.0 percent. The results from three of the LAPC xenografts are shown on the right.

FIG. 4A shows the results of equal size implants of the LAPC-4 xenograft passaged simultaneously into male (n=14) or female (n=10) mice and examined weekly for the formation of tumors. Latency is the time at which a tumor of 1 $cm^3$ was first detected. The latent period in similar experiments using males castrated prior to implantation of tumor was 14 weeks.

FIG. 4B shows the results of a cohort of 14 male mice implanted with the LAPC-4 xenograft and followed for four weeks until tumors were easily measurable. Half of the mice then underwent surgical castration to create a state of acute androgen deprivation, and tumor diameters were measured weekly. Typical results from two animals in the cohort whose tumor sizes were equivalent at 4 weeks are shown. Castration was performed at the time indicated by the arrow. The time course for tumor development in a female mouse is shown for comparison.

FIG. 4C shows the results of a cohort of 14 male mice implanted with the LAPC-4 xenograft and followed for four weeks until tumors were easily measurable. Average tumor size (+/−standard error) from the entire cohort of intact and castrated male mice is shown. The data from each animal are expressed as tumor size relative to the 4-week time point.

FIG. 9 shows the results of in vitro transcription-translation of a full length cDNA of E25a.

FIG. 15 shows average tumor size in cubic centimeters of subcutaneously implanted LNCaP cells infected with DNA encoding E25a (LnCAP-E25) or with a neomycin resistance gene (LnCAP-Neo) at 3 months after implantation.

DETAILED DESCRIPTION OF THE INVENTION

Definitions

Figure 2A:
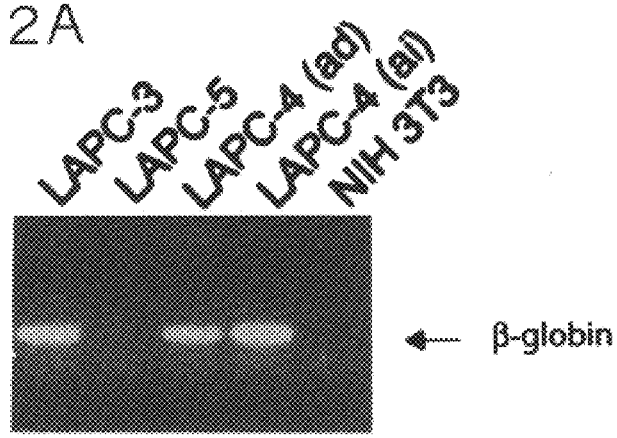
FIGS. 2A and 2B show the molecular analysis of prostate cancer xenografts for human DNA content and expression of prostate specific antigen.

As used herein, "soluble" means E25a protein not bound to a cell. For example, a portion of E25a protein fused genetically or chemically to another molecule which induces solubility, e.g., E25a protein with an Ig tail. This molecule may be biologically or chemically active.

As used herein, a molecule that is "differentially expressed" in cancer cells means a molecule that is expressed in cancer cells at a detectable level and whose expression in normal cells of the same tissue origin is significantly reduced or not detectable as compared to cancer cells. As used herein, a molecule that is "differentially expressed" in androgen independent cells means a molecule that is expressed in androgen independent cells at a detectable level and whose expression in androgen dependent cells is significantly reduced or not detectable as compared to androgen independent cells. As used herein, "significantly reduced" means that the reduction in expression is detectable by visual inspection of comparative expression data or that the reduction in expression is statistically significant.

As used herein, "measuring" includes quantitative and visual determinations of the relative amount of a substance.

As used herein, "cancer" includes both cancerous and precancerous neoplasia.

As used herein, "sample" includes samples of tissue, including biopsy specimens, or body fluids or excretions such as serum, sputum, stool or urine.

As used herein, "subject" includes human and animal subjects. Examples of animal subjects include, but are not limited to, canine, feline, equine, bovine, porcine, ovine, murine, primate, piscine and avian subjects.

As used herein, "E25a activity" means any biological activity of the E25a protein, gene or mRNA, such as, e.g., the ability to enhance tumorigenicity, to induce androgen independent growth, or to bind an antibody or other ligand directed against E25a protein.

As used herein, "androgen independent" means a cell whose survival or proliferation is not reduced by exposure to androgen, such as prostate basal cells or hormone refractory prostate cancer cells. As used herein, "androgen dependent" means a cell whose survival or proliferation is impaired by exposure to androgen, such as LNCaP cells.

As used herein "nucleic acid molecule" includes both DNA and RNA and, unless otherwise specified, includes both double-stranded, single-stranded nucleic acids, and polynucleosides thereof. Also included are hybrids such as DNA-RNA hybrids, DNA-RNA-protein hybrids, RNA-protein hybrids and DNA-protein hybrids. A nucleic acid molecule can also include modified bases as long as the modification does not significantly interfere either with binding of a ligand such as a protein by the nucleic acid or Watson-Crick base pairing.

As used herein "recombinant protein" means a protein molecule that is made using genetic engineering techniques.

As used herein "recombinant DNA" means a DNA molecule that is made using genetic engineering techniques.

As used herein "operatively linked" means to be connected to a promoter or other expression control sequence in such a way so as to enable the expression of a protein encoded by the gene sequence.

As used herein "suitable cell" means the cell is able to be transformed by a recombinant DNA using techniques in genetic engineering.

As used herein, "hormone refractory" means having growth characteristics which are not responsive to exposure to hormone, such as androgen.

Proteins of the Invention

The invention provides an E25a protein which is upregulated in cancerous cells, including cells of hormone refractory prostate cancer, colon cancer, breast cancer and other carcinomas. In one embodiment, the E25a protein is a 263 amino acid molecule and has a molecular weight of approximately 40 kd as determined by polyacrylamide gel electrophoresis (PAGE). In another embodiment, the E25a protein is a human protein. In another embodiment, the E25a protein has the amino acid sequence shown in FIG. 1. In another embodiment, the protein is a recombinant protein having an amino acid sequence substantially as shown in FIG. 1.

E25a protein molecules may be embodied in many forms. Embodiments of the E25a protein include a purified E25a protein and a functional, soluble E25a protein. The purified E25a protein molecule is substantially free of other proteins or molecules which impair the binding of E25a protein to antibody or other ligand.

One example of a functional soluble E25a protein has the amino acid sequence shown in FIG. 1 or a fragment thereof.

In one embodiment, the functional, soluble E25a protein or fragment thereof retains its ability to bind antibody or other ligand.

In accordance with the practice of this invention, E25a protein molecules of the invention may have an amino acid sequence substantially as shown in FIG. 1. For example, the sequence can have a few amino acid changes (e.g., substitutions or deletions of one or more amino acid residues) within the molecule depending on the species expressing the E25a protein. The resulting protein molecule will retain E25a activity. Amino acid substitutions include, but are not necessarily limited to, amino acid substitutions known in the art as conservative.

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

The invention also provides peptides comprising biologically active fragments of the amino acid sequence shown in FIG. 1. The peptides of the invention exhibit properties of E25a protein, such as the ability to elicit the production of antibodies which specifically bind an epitope associated with an E25a protein.

Nucleic Acid Molecules of the Invention

The invention also provides nucleic acid molecules encoding E25a protein. The nucleic acid molecules of the invention include, but are not limited to, nucleic acid molecules encoding the transmembrane domain of E25a protein. In a further embodiment, the nucleic acid molecule encodes amino acids 52–76 of FIG. 1. In one embodiment, the nucleic acid molecule is a DNA molecule. The DNA molecule may be genomic DNA or cDNA.

In one embodiment the nucleic acid molecule encoding E25a protein is the cDNA inserted into a pCRII vector (Invitrogen, Carlsbad, Calif.) and deposited under the requirements of the Budapest Treaty on Sep. 3, 1997 with the American Type Culture Collection ("ATCC"), 12301 Parklawn Drive, Rockville, Md. 20852 USA, and has been identified as ATCC Accession No.: 209233. All restrictions imposed by the depositor on the availability to the public of the deposited material will be irrevocably removed upon the granting of a patent in this U.S. application.

The invention also encompasses nucleic acid molecules that hybridize to the above-mentioned nucleic acid molecules of the invention and encode a protein having E25a activity. Such molecules can be DNA, RNA, or DNA/RNA hybrids. The hybridization can be under conventional hybridization conditions. Preferably, hybridization occurs under stringent conditions.

The invention also encompasses nucleic acid molecules that are complementary to nucleic acid molecules that encode a protein having E25a activity, such as antisense molecules or specific ribozymes which allow the control of the expression of the nucleic acid molecules of the invention in desired host and target cells. The antisense molecules and specific ribozymes are also encompassed by the invention. The antisense molecules can be RNAs or other molecules, including peptide nucleic acids (PNAs) or non-nucleic acid molecules such as phosphorothioate derivatives, that specifically bind DNA or RNA in a base pair-dependent manner.

In another embodiment, the invention relates to primers which allow the specific amplification of nucleic acid molecules of the invention or of any specific parts thereof. In another embodiment, the invention relates to probes that specifically hybridize to nucleic acid molecules of the invention or to any part thereof. The nucleic acid probes can be labeled with a detectable marker. Examples of a detectable marker include, but are not limited to, a radioisotope, a fluorescent compound, a bioluminescent compound, a chemiluminescent compound, a metal chelator or an enzyme.

Vectors

The invention further provides an expression vector comprising a recombinant DNA molecule encoding an E25a protein.

The invention provides a host-vector system comprising a vector encoding an E25a protein in a suitable host cell. The vector can be operatively linked to a promoter. Preferably, the suitable cell is a bacterial cell or a eucaryotic cell. An example of a compatible eucaryotic host cell is an LNCaP cell.

In accordance with the practice of the invention, the vector can be a plasmid, cosmid or phage vector encoding the cDNA molecule discussed above. Additionally, the invention provides a host-vector system comprising the plasmid, cosmid or phage vector transfected into a suitable eucaryotic host cell. Examples of suitable eucaryotic host cells include a yeast cell, a plant cell, or an animal cell, such as a mammalian cell. The host-vector system is useful for the production of an E25a protein. Alternatively, the host cell can be a prokaryote, such as a bacterial cell.

Alternatively, a vector encoding E25a protein can be useful for infecting a host cell to induce tumorigenicity and/or androgen independent growth. A host cell so infected can be used in a screening assay for identifying therapeutic agents useful for treating diseases associated with expression of an E25a nucleic acid molecule, including, e.g., hormone refractory prostate cancer.

Methods of Producing E25a Protein

The invention provides a method of producing an E25a protein. The method comprises growing a host-vector system of the invention so as to produce the E25a protein and recovering the E25a protein so produced. Protein recovery can be effected using standard methodologies.

By use of the above method, it is possible for the host-vector system to synthesize the E25a proteins of the invention in culture in large quantities.

The invention further provides a method of producing an E25a protein in vitro. This method comprises transcribing a vector comprising a nucleic acid molecule encoding an E25a protein in the presence of transcribable RNA, thereby creating mRNA. Additionally, the method requires translating the mRNA transcribed in the above step so as to provide E25a protein. As a final step, the E25a protein is recovered.

Antibodies

The invention further provides antibodies that specifically bind to an E25a protein (E25a antibodies). In one embodiment, the antibodies specifically bind to the extracellular domain of an E25a protein. In another embodiment, the antibodies specifically bind to the intracellular domain of an E25a protein. The antibodies may be polyclonal or monoclonal. The invention also encompasses antibody fragments which specifically recognize an E25a protein, the extracellular domain of an E25a protein or the intracellular domain of an E25a protein. As used herein, an antibody fragment is defined as at least a portion of the variable region of the immunoglobulin molecule which binds to its target, i.e., the antigen binding region. Some of the constant region of the immunoglobulin may be included.

The polyclonal antibodies of the invention can be produced by conventional techniques. These antibodies can be used for immunoprecipitation and western blotting.

The monoclonal antibody of the invention can be produced using well-established hybridoma techniques first introduced by Kohler and Milstein [see, Kohler and Milstein, 1975. See, also, Brown et al., 1981; Brown et al., 1980; Yeh et al., 1979; and Yeh et al., 1982].

These techniques involve the injection of an immunogen (e.g., cells or cellular extracts carrying the antigen or purified antigen) into an animal (e.g., a mouse) so as to elicit a desired immune response (i.e., antibodies) in that animal. After a sufficient time, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of a number of myeloma cell lines may be used as a fusion partner according to standard techniques; for example, the P3-NS1/1Ag4-1, P3-x63-Ag8.653 or Sp2/0 Ag14 myeloma lines. These myeloma lines are available from the American Type Culture Collection ("ATCC") in Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting conditions to obtain isolated clones. The supernatants of the hybridomas are screened for the presence of antibody of that desired specificity, e.g., by immunoassay techniques using the antigen that had been used for immunization. Positive clones can then be subcloned under limiting dilution conditions and the monoclonal antibody produced can be isolated. Hybridomas produced according to these methods can be propagated in vitro or in vivo (in ascites fluid) using techniques known in the art (see, generally, Fink et al., supra at page 123, FIGS. 6–11].

Commonly used methods for purifying monoclonal antibodies include ammonium sulfate precipitation, ion exchange chromatography, and affinity chromatography [see, e.g., Zola et al., "Techniques For The Production And Characterization Of Monoclonal Hybridoma Antibodies", in *Monoclonal Hybridoma Antibodies: Techniques and Applications*, Hurell (ed.), pp. 51–52 (CRC Press 1982)].

The antibody or fragment thereof of the invention may be labeled with a detectable marker. Suitable detectable markers include, but are not limited to, a radioisotope, a fluorescent compound, a bioluminescent compound, chemiluminescent compound, a metal chelator or an enzyme.

The antibody or fragment thereof of the invention can be useful for detecting the presence of cancer, including carcinomas such as carcinoma of the breast, colon or prostate, including hormone refractory prostate cancer.

The antibody or fragment thereof of the invention can be useful for inhibiting the activity of an E25a protein, thereby inhibiting tumor cell proliferation and/or conversion of a cell from androgen dependence to androgen independence. The antibody can be conjugated to a second molecule, such as a cytotoxic agent, and used for targeting the second molecule to an E25a protein positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid.

Techniques for conjugating therapeutic agents to antibodies are well known (see, e.g., Arnon et al.; Reisfeld et al., 1985; Hellstrom et al.; Robinson et al., 1987; Thorpe, 1985; and Thorpe et al., 1982).

Methods of the Invention

The invention provides a method of inhibiting the expression of E25a gene in a cell comprising introducing the complementary nucleic acid molecule of the invention, such as an antisense molecule, into the cell so that the nucleic acid molecule binds at least a portion of an endogenous nucleic acid molecule encoding E25a protein. The binding of the nucleic acid molecule to the endogenous nucleic acid molecule encoding E25a protein inhibits the expression of an E25a nucleic acid molecule.

The invention further provides a method of inhibiting the proliferation of tumor cells comprising introducing the complementary nucleic acid molecule of the invention, such as an antisense molecule, into the cell so that the nucleic acid molecule binds at least a portion of an endogenous nucleic acid molecule encoding E25a protein. The binding of the nucleic acid molecule to the endogenous nucleic acid molecule encoding E25a protein inhibits, directly or indirectly, the proliferation of tumor cells and/or progression from androgen dependence to androgen independence. In one embodiment, the tumor cells are carcinoma cells. By way of example, the carcinoma cells can be derived from prostate, colon or breast. In one embodiment, the tumor cells are hormone refractory prostate cancer cells.

The invention further provides a method of treating cancer comprising administering to a subject the complementary nucleic acid molecule of the invention, such as an antisense molecule, in an amount sufficient to inhibit proliferation of tumor cells, thereby treating the cancer. In one embodiment, the tumor cells are carcinoma cells. By way of example, the carcinoma cells can be derived from prostate, colon or breast. In one embodiment, the tumor cells are hormone refractory prostate cancer cells.

The invention further provides a method of inhibiting the activity of E25a protein in a cell comprising contacting an E25a antibody with the cell so that the antibody binds an endogenous E25a protein. The binding of the antibody to the endogenous E25a protein inhibits the activity of E25a protein. In one embodiment, the cells are carcinoma cells. By way of example, the carcinoma cells can be derived from prostate, colon or breast. In one embodiment, the cells are hormone refractory prostate cancer cells.

The invention further provides a method of inhibiting the proliferation of tumor cells comprising contacting an E25a antibody with the cell so that the antibody binds an endogenous E25a protein. The binding of the antibody to the endogenous E25a protein inhibits the proliferation of tumor cells. In one embodiment, the tumor cells are carcinoma cells. By way of example, the carcinoma cells can be derived from prostate, colon or breast. In one embodiment, the tumor cells are hormone refractory prostate cancer cells.

The invention further provides a method of treating cancer comprising administering to a subject an E25a antibody in an amount sufficient to inhibit proliferation of tumor cells, thereby treating the cancer. In one embodiment, the tumor cells are carcinoma cells. By way of example, the carcinoma cells can be derived from prostate, colon or breast. In one embodiment, the tumor cells are hormone refractory prostate cancer cells.

In another embodiment, the invention provides a method of treating cancer comprising administering to a subject the antibody of the invention conjugated or linked to a second molecule. The second molecule can be a therapeutic drug or a cytotoxic agent. Examples of cytotoxic agents include, but are not limited to, ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid.

The invention further provides a method of detecting the presence of cancer in a sample from a subject, including hormone refractory prostate cancer, colon cancer, breast cancer or other carcinomas. The method comprises determining the amount of E25a protein present in the sample. The amount of E25a protein so determined is compared with the amount present in a sample from a normal subject. The presence of a significantly different amount indicates the presence of cancer. In one embodiment, the method comprises contacting an E25a antibody with a sample and detecting binding of the antibody to an E25a protein in the sample. In one embodiment, the cancer is hormone refractory prostate cancer. In another embodiment, the cancer is derived from colon, breast or another epithelial tissue. The antibody may be detectably labeled, as discussed above. The detection may be by immunocytochemistry, immunoblot such as dot-blot or western blot, enzyme histochemistry, autoradiography or other detection techniques known in the art.

The invention further provides a method of detecting the presence of cancer in a sample from a subject, including hormone refractory prostate cancer, colon cancer, breast cancer or other carcinomas. The method comprises determining the amount of RNA encoding E25a protein present in the sample. The amount of RNA encoding E25a protein so determined is compared with the amount present in a sample from a normal subject. The presence of a significantly different amount indicates the presence of cancer. In one embodiment, the determination comprises isolating the RNA present in the sample and contacting the RNA so isolated with a first nucleic acid molecule which is complementary to a second nucleic acid molecule encoding E25a protein under conditions sufficient to permit hybridization of the complementary first nucleic acid molecule with the RNA. The determination further comprises measuring the amount of RNA so hybridized, thereby determining the amount of RNA encoding E25a protein present in the sample. The amount of hybridized RNA is proportional to the amount of RNA encoding E25a protein present in the sample.

In another embodiment, the determination comprises isolating the RNA present in the sample and contacting the RNA so isolated with a first nucleic acid molecule which is complementary to a second nucleic acid molecule encoding E25a protein under conditions sufficient to permit the formation of a complementary nucleic acid molecule/RNA complex. The determination further comprises isolating the complex so formed and measuring the amount of complex, thereby determining the amount of RNA encoding E25a protein present in the sample. The complex can be isolated, for example, by exposing the contacted RNA and complementary nucleic acid molecule to an enzyme that digests uncomplexed nucleic acids, such as S1 nuclease, so that complementary nucleic acid molecule/RNA complex remains. The amount of complex is proportional to the amount of RNA encoding E25a protein present in the sample. Methods for quantitative determinations using reverse transcriptase polymerase chain reaction (RT-PCR) are described in U.S. Pat. No. 5,639,606, issued Jun. 17, 1997, the contents of which are hereby incorporated by reference.

In another embodiment, the determination comprises isolating the RNA present in the sample and contacting the RNA so isolated with a first nucleic acid primer which is complementary to a mRNA molecule encoding E25a protein under conditions sufficient to permit the formation of a first complementary DNA strand. The conditions can include, for example, the presence of nucleotides and a suitable enzyme such as reverse transcriptase. The determination further comprises contacting the first complementary DNA strand so formed with a second nucleic acid primer which is complementary to the first complementary DNA strand under conditions sufficient to permit the formation of a second complementary DNA strand. The condition can include, for example, the presence of nucleotides and a suitable enzyme such as polymerase, e.g., Taq polymerase. The determination further comprises amplifying the first and second complementary DNA strands and measuring the amount of each of the complementary DNA strands so amplified, thereby determining the amount of RNA encoding E25a protein present in the sample. The amount of first and second complementary DNA strands is proportional to the amount of RNA encoding E25a protein present in the sample.

In one embodiment, the cancer is hormone refractory prostate cancer. In another embodiment, the cancer is derived from colon, breast or another epithelial tissue. The complementary nucleic acid molecule, or probe, may be detectably labeled, as discussed above. The sample may be prepared for detection by conventional techniques, including reverse transcriptase polymerase chain reaction (RT-PCR), northern blot, S1 nuclease analysis, and in situ hybridization. The detecting may be by enzyme histochemistry, autoradiography or other detection techniques known in the art.

The methods described herein for detecting cancer can be useful for diagnosing hormone refractory (androgen independent) prostate cancer. This ability to distinguish hormone refractory from androgen responsive cancer permits a clinician to adjust a subject's treatment accordingly. For example, in the event that a subject's prostate cancer has become androgen independent, the treating clinician can avoid androgen ablation therapy and adopt a more appropriate treatment protocol.

The invention additionally provides screening assays for identifying therapeutic agents useful for treating diseases associated with expression of an E25a nucleic acid molecule, including, e.g., hormone refractory prostate cancer. The assay comprises infecting a host cell with a vector encoding E25a protein so as to induce proliferation and/or androgen independent growth. The method further comprises contacting an agent of interest with the host cell so infected and determining whether the agent inhibited proliferation and/or androgen independent growth, thereby identifying agents useful for treating diseases associated with expression of an E25a nucleic acid molecule.

Compositions

The invention provides a pharmaceutical composition comprising an E25a nucleic acid molecule of the invention or an expression vector encoding an E25a protein or encoding a fragment thereof and, optionally, a suitable carrier. The invention additionally provides a pharmaceutical composition comprising an E25a antibody or fragment thereof which recognizes and binds an E25a protein. In one embodiment, the antibody or fragment thereof is conjugated or linked to a therapeutic drug or a cytotoxic agent.

Suitable carriers for pharmaceutical compositions include any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The invention also provides a diagnostic composition comprising an E25a nucleic acid molecule of the invention, a probe that specifically hybridizes to a nucleic acid molecule of the invention or to any part thereof, or an E25a antibody or fragment thereof. The nucleic acid molecule, the probe or the antibody or fragment thereof can be labeled with a detectable marker. Examples of a detectable marker include, but are not limited to, a radioisotope, a fluorescent compound, a bioluminescent compound, a chemiluminescent compound, a metal chelator or an enzyme.

Advantages of the Invention

The invention provides molecules useful for the detection of cancer, including cancer of the prostate, colon, breast and other epithelial tissues. In one embodiment, the molecules of the invention can be used to distinguish hormone refractory prostate cancer. In another embodiment, the molecules of the invention can be used to distinguish advanced stage cancer cells. The ability to distinguish hormone refractory prostate cancer or advanced stage cancer permits the development of a treatment strategy appropriate to the type of cancer involved. For example, in the event that a subject's prostate cancer has become androgen independent, the treating clinician can avoid androgen ablation therapy and adopt a more appropriate treatment protocol.

In addition, the invention provides molecules useful as targets for therapeutic agents. Anti-cancer therapeutic agents can be targeted to cells differentially expressing an E25a nucleic acid molecule to facilitate treatment of metastatic cancer, such as hormone refractory prostate cancer. Because expression of an E25a nucleic acid molecule can induce tumorigenicity and confer androgen independence on previously androgen dependent cells, molecules directed against E25a protein or nucleic acid molecules which encode E25a protein can be useful for inhibition of tumor cell proliferation and for treatment of cancer, including carcinoma of the colon or breast or hormone refractory prostate cancer.

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

EXAMPLE 1

Progression of Metastatic Human Prostate Cancer to Androgen Independence in SCID Mice The data herein show reproducible propagation of explants (xenografts) from patients with advanced stage prostate cancer in severe combined immune deficient (SCID) mice models. These xenografts can be expanded in sufficient quantity to facilitate certain molecular and biochemical investigations. In addition, certain xenografts retain the desired characteristics of progression from androgen dependent to androgen independent disease and metastasis to hematopoietic tissues. These models are powerful new tools to study the pathogenesis and treatment of advanced prostate cancer because they accurately recapitulate the clinical biology of the disease.

METHODS

Patients

All clinical material was obtained from patients with locally advanced or metastatic (stage C or D) prostate cancer after obtaining informed consent according to an IRB approved protocol. Most patients had undergone some form of androgen ablation therapy (medical or surgical) and shown progressive disease at the time the tissue samples were obtained. One patient (LAPC-7) had not been previously treated.

Animals

SCID (C.B.-17 scid/scid) mice were bred and maintained in a laminar flow tower in a defined flora colony at UCLA as described previously (Aldrovoni et al., 1993). Clinical material obtained at the time of surgery was placed on ice and immediately transferred to the SCID mouse facility for implantation. A scalpel was used to mince the tissue into 2–3 mm sections which were implanted surgically into the subcutaneous tissue in the flanks of SCID mice. Mice were anesthetized with metaphane prior to implantation. All initial implants were performed with 100–200 µl of Matrigel (Collaborative Research) injected around the prostate cancer implant. Once a xenograft was passaged 2–3 times, Matrigel was no longer used for serial propagation. Androgen ablation was performed by surgical castration under anesthesia. Tumor sizes were determined by weekly caliper measurements of height, width and depth.

PCR Assays—Histology and Immunohistochemistry

DNA from tumor tissue was prepared using SDS detergent extraction and proteinase K digestion as described (Sambrook et al., 1989) RNA was prepared using a commercially available kit containing guanidine thiocyanate and b-mercaptoethanol (RNAgents Total RNA Isolation System from Promega). All surgical instruments used at the time of necropsy were cleaned by repeated rinses in HCl, DEPC treated $H_2O$ and ethanol to avoid contamination across tissue preps. DNA-PCR assays for human β-globin (Aldrovoni et al., 1993; Saiki et al., 1985) and RT-PCR assays for PSA (Pang et al., 1995) were performed as previously described. The quality of RNA samples was confirmed by ethidium bromide staining for ribosomal RNA and by RT-PCR using primers for b-actin (Pang et al., 1995) as a control. Details on the primer sequences can be found in the original references. Immunohistochemical staining using polyclonal antisera to PSA (Dako) was performed as described (Hsu et al., 1981)

Cytogenetics

Tumor tissue was aseptically transported in DMEM growth medium supplemented with 10% fetal bovine serum by overnight courier to the University of Utah for cytogenetic preparation and analysis. Briefly, tissue was minced and washed in Hanks Balanced Salt Solution ($Ca^{++}$ and $Mg^{++}$ free), resuspended in RPMI medium supplemented with lot fetal bovine serum, and cells were arrested in metaphase with 0.001 µg/ml colcemid for 16 hours. Cytogenetic harvests were done using standard procedures, and following hypotonic (0.075M) KC treatment and 3:1 methanol/acetic acid fixation, slides were prepared and chromosomes G-banded with trypsin/Wrights stain.

RESULTS

Surgical Explants from Advanced Stage Prostate Cancer can be Serially Propagated in SCID Mice.

Biopsies of locally advanced or metastatic tumor tissue were obtained from 8 patients with locally advanced or metastatic (stage C, D1 or D2) prostate cancer who underwent palliative surgical procedures due to complications from disease. Biopsy material was immediately transferred from the surgical suite to the SCID mouse facility, minced into two 3 mm sections and implanted subcutaneously into SCID mice in the presence of Matrigel, an extracellular matrix preparation previously shown to enhance the growth of epithelial tumors in vivo (Noel et al., 1992), including prostate cancer cells and cell lines (Pretlow et al., 1991; Lim et al., 1993). Tumor growth was scored positive only if the explant showed a sustained two-three threefold increase in size. In addition to histologic studies, two molecular assays were performed on each xenograft to verify the human origin of the tumors. These include a PCR assay on genomic DNA using primers specific for the human β-globin gene and a quantitative RT-PCR assay on RNA from tumors using primers specific for the human PSA gene. The PSA expression assay was also used to verify the prostatic origin of the xenografts.

Explants from six of eight patients (named LAPC 1-8 for <u>L</u>os <u>A</u>ngeles <u>P</u>rostate <u>C</u>ancer) formed tumors after a latent period which varied from 2–10 months (summarized in Table 1). The six explants which grew were passaged into secondary recipients in an attempt to establish permanent xenografts. Two of these (LAPC-1 and LAPC-5) were terminated after 3–4 passages because we were unable to detect human DNA or expression of PSA in the tumors. These explants perhaps were overgrown by cells of murine origin because they contained human DNA content and expressed PSA during early passages of LAPC-5 (Table 1, column 6,7).

TABLE 1

Summary of Advanced Prostate Cancer[1] Implants into SCID Mice

| Patient Implant (disease stage) | Biopsy site | Growth | Time interval for tumor growth | Passages | Human DNA Status[2] | PSA Status[3] | Notes |
|---|---|---|---|---|---|---|---|
| LAPC-1 (stage D) | liver met | yes | 2 months | 5 | negative on passage | negative | overgrowth by tumor of murine origin after serial passage |
| LAPC-2 (stage D) | lymph node met | no | no growth at 2 years | 1 | — | — | — |
| LAPC-3 (stage D) | prostate-channel TURP | yes | 10 months | 3 | positive | positive | no PSA positive cells outside site of implantation (n = 2) |
| LAPC-4 (stage D) | lymph node met | yes | 3 months | >8 | positive | positive | PSA positive cells in bone marrow, spleen, blood in 50% of mice (n = 12) |
| LAPC-5 (stage D) | lymph node met | yes | 9 months | 5 | positive, then negative on passage 4 | positive, then negative on passage 4 | overgrowth by tumor of murine origin on passage 4 |
| LAPC-6 (stage C) | prostate | no | no growth at 9 months | 1 | — | — | — |
| LAPC-7 (stage C) | prostate | yes | 3 months | 2 | positive | negative | — |
| LAPC-8 (stage D) | lymph node met | yes | 10 months | 2 | positive | positive | no PSA positive cells outside implantation site (n = 1) |

[1]locally advanced (stage C) or nietastatic (stage D) disease;
[2]determined by PCR of genomic DNA for human β-globin;
[3]determined by RT-PCR and/or immunohistochemistry The remaining four explants (LAPC-3,4,7 and 8) were positive for human β-globin DNA at first passage, and LAPC-3 and LAPC-4 have remained consistently positive after 3 and 8 passages, respectively (FIG. 2A). We used a previously developed RT-PCR assay (Pang et al., 1995) to measure the levels of PSA mRNA expression in comparison to LNCaP, a prostate cancer cell line known to synthesize PSA mRNA and protein (Hotoszewicz et al., 1983). This assay is semi-quantitative and is capable of detecting PSA mRNA expression from 100 LNCaP cells diluted into $10^5$ mouse cells (1 in 1000 or 0.1 percent) (FIG. 2B, top panel).

Figure 2B:
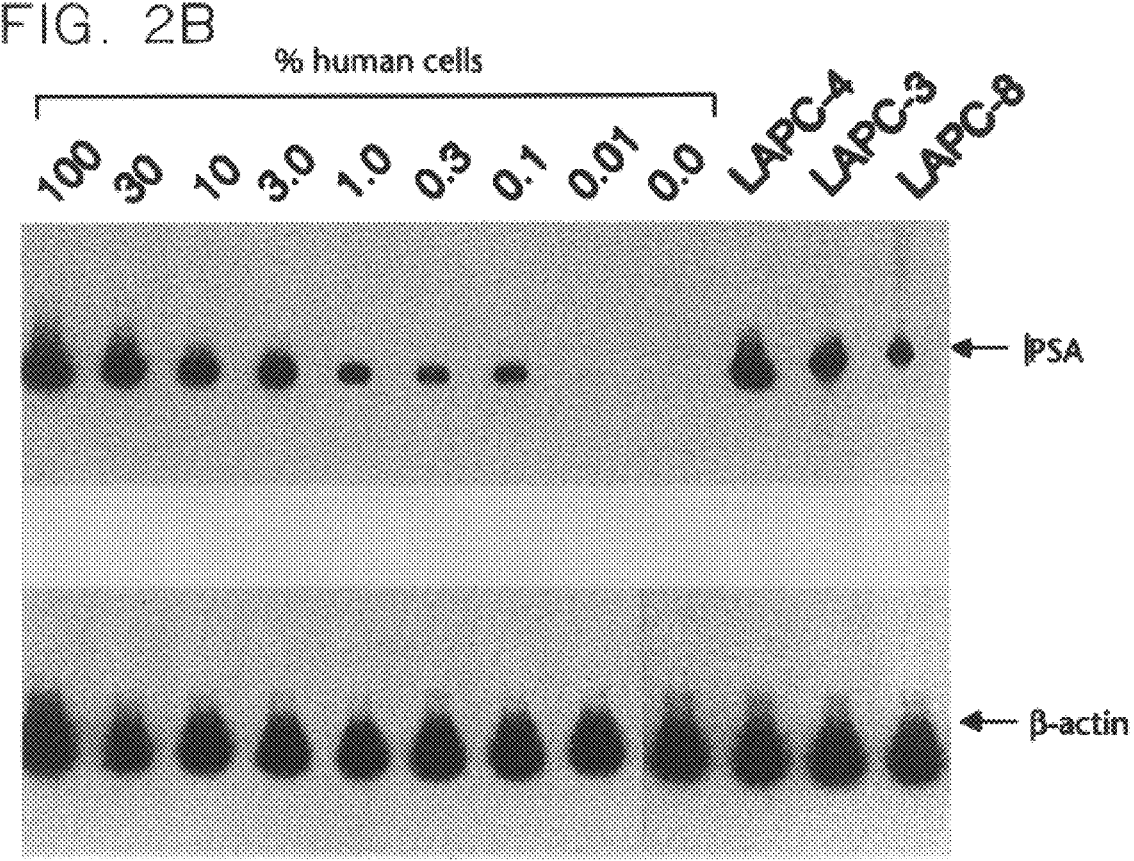

Three of the four xenografts (LAPC-3,4,8) expressed human PSA at levels which varied from 1 to 100 percent of the level found in LNCaP cells (FIG. 2B, top panel). Simultaneous RT-PCR analysis using primers for β-actin confirmed that equivalent levels of RNA were present in each reaction (FIG. 2B, bottom panel).

Figure 3:
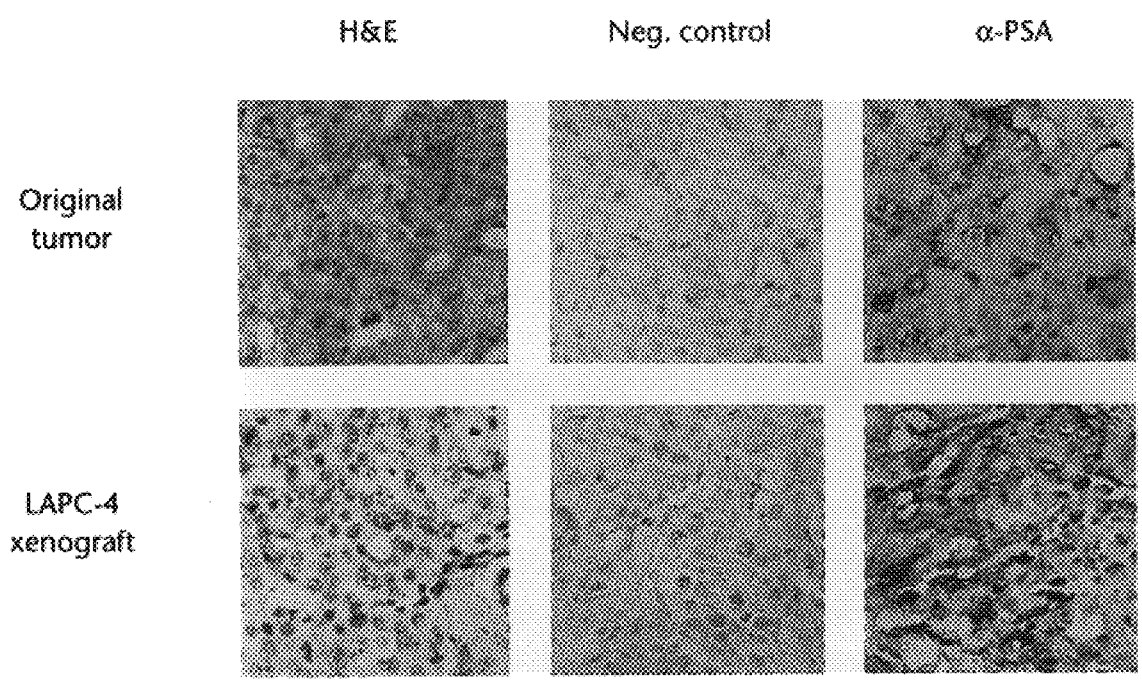
FIG. 3 shows immunohistochemical analysis of the LAPC-4 xenograft which shows expression of prostate specific antigen. Paraffin sections of formalin fixed tissue from the original tumor sample obtained at the time of surgery (top row) and the LAPC-4 xenograft (bottom row) were stained with hematoxylin and eosin (left), a control antibody (middle) and an antibody specific for human PSA (right).

FIG. 3 histologically compares the original LAPC-4 tumor sample obtained at the time of surgery to the same tumor after passage as a xenograft in male mice. The hematoxylin and eosin stained sections (FIG. 3, left panels) show a monotonous population of anaplastic cells which stain positive for PSA using immunohistochemical analysis (FIG. 3, right panels). These findings demonstrate that advanced stage prostate cancer explants can be serially propagated in SCID mice and retain definitive tissue specific gene expression.

Karyotype Analysis of Prostate Cancer Xenografts Reveals Novel Structural and Numerical Chromosome Abnormalities Extensive cytogenetic studies of human prostate cancer have been difficult due to heterogeneity of clinical material obtained at surgery and limited growth of prostate tumor cells in vitro. To determine if passage of prostate tumor tissue in SCID mice might facilitate karyotypic analysis, we analyzed early passage tumors from the LAPC-3 and LAPC-4 xenografts using standard cytogenetic techniques. A high mitotic yield was obtained from tumor samples from both xenografts and all metaphase cells contained human chromosomes. Detailed composite karyotypes are noted in Table 2. A total of 80 metaphases were counted from three independent LAPC-3 tumors obtained at passage 2 and 3 and showed a range of 68–81 chromosomes per cell. The modal chromosome number was 69, which suggests that this line is near-triploid, yet the presence of four copies of many chromosomes raises the possibility of reduction from tetraploid. Structural and numerical changes were observed in all cells. Two third passage LAPC-4 tumors were analyzed and showed a range of 76–92 chromosomes per cell from 44 metaphases. The modal chromosome number was 89, suggesting a hypotetraploid line. Both xenografts show previously reported numerical and structural chromosome abnormalities such as loss of Y and 16. In addition, both xenografts contain a deletion at chromosome 12p12, a karyotypic abnormality that has not been previously reported in prostate cancer.

TABLE 2

Cytogenetic Analysis of Human Prostate Cancer Xenografts

| Xenograft | Passage number at time of analysis (number of independent tumors) | Number of metaphases analyzed | Modal Chromosome Number | Karyotype |
|---|---|---|---|---|
| LAPC-3 | passage 2 (1 tumor); passage 3 (2 tumors) | 80 | 69 | 68–81, XXY + add(1)(p22), −2, +3, +4, +5, del(6)(q21)x2, +7, +9, +9, −11, del(12)(p12), −13, −13, +14, t(14;14)(q10;q10), −16, +18, +19, +20 [cp80] |
| LAPC-4 | passage 3 (2 tumors) | 44 | 89 | 76–92, XX, −Y, −Y, add(8)(p23), +9, del(12)(p12), −14, −16, −18, −21, +mar1, +mar2 [cp44] |

The Transition from Androgen Dependent to Independent Growth is Modeled in Prostate Cancer Xenografts Prostate cancer cells are exquisitely sensitive to the growth stimulatory effects of androgen, but androgen independent disease eventually develops in patients under the selective pressure of androgen deprivation. The mechanism for this transition to androgen independent growth is unknown. The LAPC-4 xenograft was used to determine if this phase of the disease could be modeled in SCID mice. The LAPC-4 xenograft reproducibly forms tumors on serial passages (currently at passage 8) in male mice with 100 percent frequency.

Figure 4A:
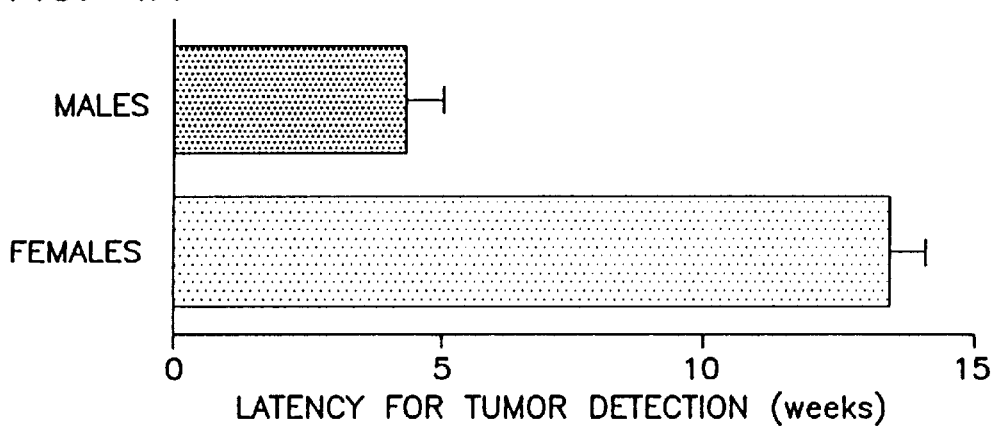
FIGS. 4A–4C demonstrate that LAPC-4 is androgen dependent, but that androgen independent tumors can be derived by passage into females or castrated males or by castration of males.

The androgen dependence of the xenograft was measured in vivo in two ways. First the growth rates after implantation in intact male mice was compared to growth rates in castrated male or female mice. The average time for tumor formation in castrate male mice or female mice (n=10) was 13.4 weeks versus 4.3 weeks in intact males (n=14) (FIG. 4A). The androgen independence of tumors growing in female or castrated male mice was confirmed by secondary transfer experiments. Once established, such tumors grew within 4–5 weeks regardless of the hormonal background of the recipient mouse.

Figure 4B:
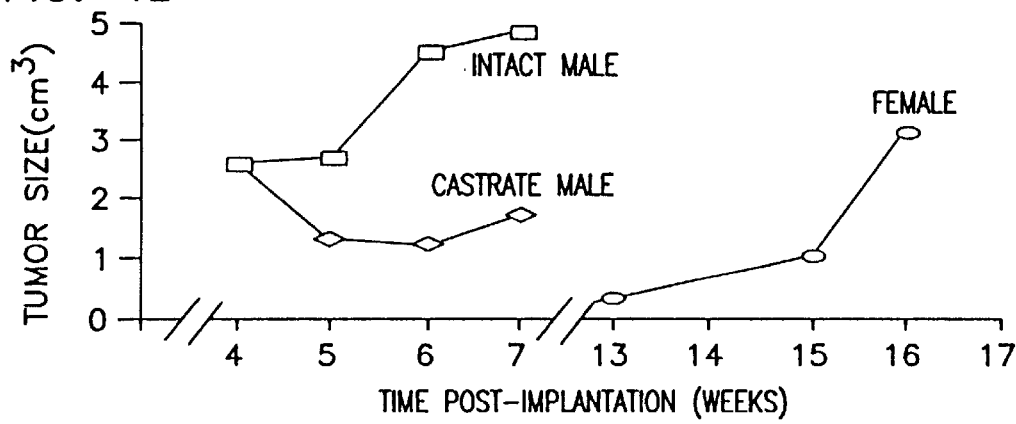
Figure 4C:
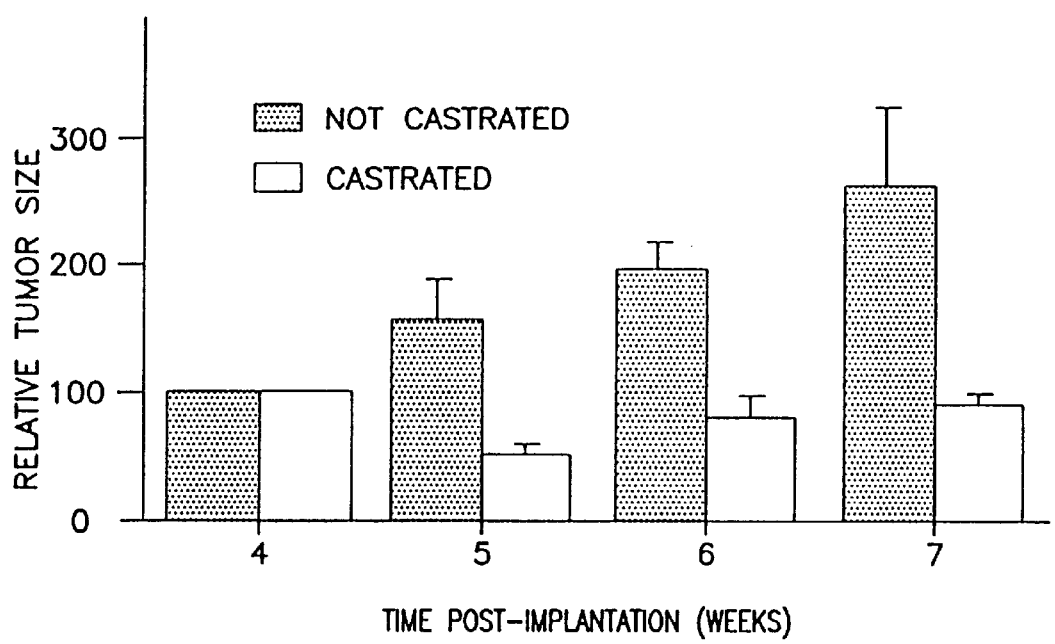

Clinically, anti-androgen therapy causes temporary regression of disease in most patients with advanced prostate cancer. To determine if a similar phenomenon is observed in the mouse model, the effect of acute androgen deprivation on established tumors growing in male mice was examined. Equivalent size implants of the LAPC-4 xenograft were passaged into a cohort of 14 male mice, all of which developed easily measurable tumors after four weeks. Half of these mice underwent castration, then the tumor sizes in each group were determined weekly by caliper measurement of tumor diameters in three dimensions. Tumors in the uncastrated mice doubled in size over a 2–3 week period (FIGS. 4B,C). In contrast, the castrated mice showed a decrease in tumor size at one week of approximately 50 percent which persisted for 2–3 weeks. These tumors resumed growth after a variable latent period (3–8 weeks) and eventually grew to the same size seen in uncastrated mice. These results show that the LAPC-4 xenograft displays androgen dependent growth, that androgen independent sublines can be developed, and that this xenograft recapitulates the clinical transition from androgen sensitive to androgen independent disease.

Micrometastatic Disease is Detected in Mice Bearing the LAPC-4 Xenograft

Figure 5:
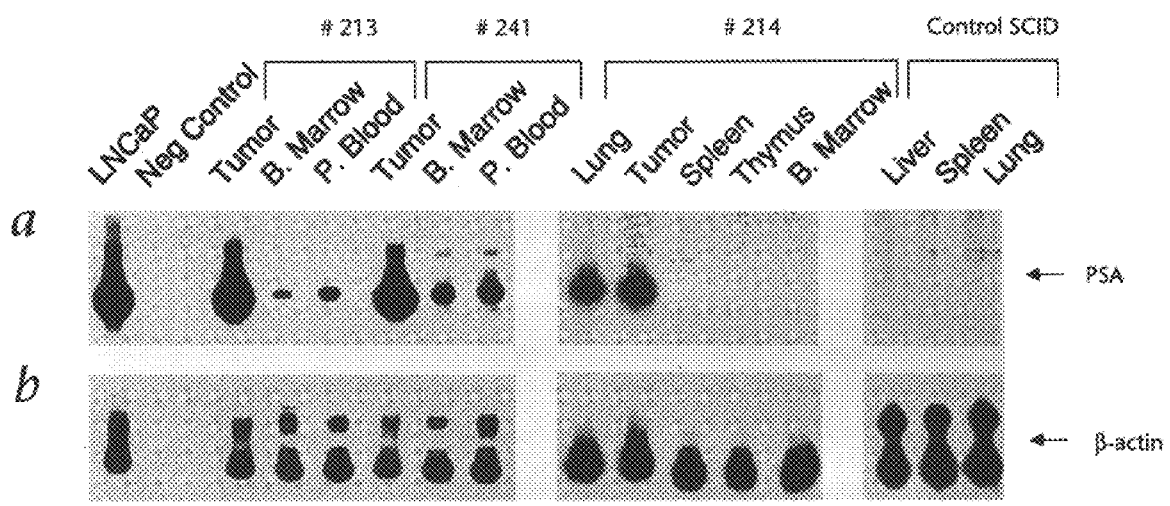
FIGS. 5(A–B) shows detection of micrometastatic disease in mice bearing LAPC-4 xenografts. Total RNA was isolated from the murine tissues indicated and analyzed for expression of PSA (panel A) or β-actin (panel B) using RT-PCR. The results from the tumor and various tissues of three representative mice (#213, #241, and #214) are shown. Tissues from a fourth mouse (control SCID) were analyzed as a negative control. The signal can be quantified by comparison with LNCaP (lane 1, see also FIG. 2). No RNA was added to the negative control sample (lane 2).

In patients with advanced stage disease, prostate cancer cells metastasize to pelvic lymph nodes and bone and can be detected in peripheral blood and bone marrow using RT-PCR assays for PSA mRNA (Ghossein et al., 1995; Seiden et al., 1994; Wood et al., 1994; Katz et al., 1994). The LAPC-4 xenograft was derived from a lymph node containing metastatic prostate cancer cells. The metastatic potential of this xenograft was examined by analyzing peripheral blood, bone marrow, spleen, liver, lung and kidney tissue from mice implanted with subcutaneous tumors for the presence of prostate cancer cells outside the site of implantation. Examples of the analysis from three mice (FIG. 5A) demonstrate detection of PSA mRNA in blood and bone marrow of two mice (mouse #213, #241) and in the lung of a third mouse (mouse #214). Simultaneous RNA-PCR studies using $\beta$-actin primers confirmed equivalent RNA loading (FIG. 5B). To confirm that these positive PSA mRNA signals were not due to contamination with tumor cells during the necropsy procedure or the preparation of RNA, samples were simultaneously prepared from a control mouse which was not implanted with a xenograft. No PSA expression was detected in control animals, even after prolonged autoradiography exposure times (FIG. 5A, right panel). The results from 12 animals bearing LAPC-4 xenografts (Table 3) show that 50 percent of mice have PSA mRNA positive cells (level of PSA expression by RT-PCR of 0.1 percent or greater) detected in peripheral blood, bone marrow or spleen. The level of expression was roughly quantitated by comparison to a series of LNCaP cells diluted into murine fibroblasts (refer to FIG. 2B) and varied from 0.1% to 10%. It is of interest that the frequency of detecting micrometastatic disease was higher (80%) in female mice or in male mice castrated prior to implantation compared to intact males (27%). These results require confirmation in a larger number of mice but suggest that the transition to androgen independent disease is associated with a higher metastatic rate, a hypothesis which is also supported by clinical experience.

TABLE 3

Frequency of Detection of PSA positive cells in Hematopoietic Tissues of LAPC-4 bearing SCID Mice

|  | # of mice with PSA positive cells in hematopoietic organs per total # analyzed |
|---|---|
| Intact Males | 2/7 (29%) |
| Castrate Males (or Females) | 4/5 (80%) |
| Total | 6/12 (50%) |

Mechanistic studies of prostate cancer progression require models which recapitulate the clinical biology of the disease. Two key events occur in the evolution from early to late stage prostate cancer which are responsible for most disease-related morbidity and mortality. These include the metastasis of cancer cells from the local environment of the prostate gland to regional lymph nodes and bone and the transition from androgen sensitive to androgen independent growth. The results disclosed herein demonstrate that explants from patients with advanced prostate cancer grow and passage in SCID mice with high frequency and retain characteristics of human prostate cancer. These data also show that metastasis and progression to androgen independence can be modeled in this system.

Routine cytogenetic studies of prostate cancer are problematic due to difficulties in obtaining metaphase preparations from tumor samples, primarily because these tumors fail to grow easily in vitro. The results disclosed herein demonstrate that cytogenetic information can be readily obtained from prostate tumors passaged in SCID mice. The two xenografts analyzed to date show karyotypic changes that have previously been reported in primary prostate cancer such as tetraploidy and loss of Y (Brothman et al., 1990; Debruyne et al., 1993; Micale et al., 1993). The novel structural abnormalities observed, such as deletion at 12p12, deletion at 6q21 and t (14; 14) (q10; q10), may provide important clues toward genetic events in prostate cancer progression. The 12p12 deletion is of particular interest since it is present in two independent xenografts derived from two different patients. The biological relevance of these changes may be determined by defining their frequency in more xenografts and by directly analyzing clinical material using molecular probes from these regions.

The LAPC-4 xenograft is of particular interest because it models the transition from androgen dependent to androgen independent disease and the development of micrometastatic disease. Tumors passaged in male mice retain androgen dependent growth characteristics, whereas tumors passaged in castrated males or female mice acquire a stable androgen independent phenotype. These sublines can be easily expanded to provide ample tissue for molecular and biochemical analysis of events associated with androgen independent growth. There are few other experimental models for androgen dependent prostate cancer growth. Published reports include the widely used LNCaP cell line (Lim et al., 1993; Gleave et al., 1992) and two recently described xenografts, CWR22 (Weinstein et al., 1994) and LuCaP23 (Lin et al., 1996). The LAPC-4 xenograft is unique because tumors placed under the selective pressure of androgen deprivation reproducibly evolve to an androgen independent state, providing an opportunity to evaluate the molecular changes associated with androgen independence over time and directly test their functional importance.

EXAMPLE 2
Isolation of Genes which are Differentially Expressed in Androgen Dependent Versus Androgen Independent Disease using Representational Difference Analysis (RDA)

The following experiments utilized the SCID mouse model to search for genes which are differentially expressed during the transition to androgen independence since such genes might be critical regulators of androgen independent growth (i.e., they might cause or enable androgen independent growth).

Specifically, we used a PCR-based subtractive hybridization technology known as representational difference analysis (RDA) to isolate cDNAs which are selectively expressed in androgen responsive (AR) or androgen independent (AI) tumors (Braun et al., 1995).

The procedure requires the synthesis of small amounts of cDNA (~1 μg) from the two populations to be compared (in this case, AR and AI). The cDNA was digested, ligated to a unique set of adapters, amplified, and subtracted (see FIG. 6).

Figure 6:
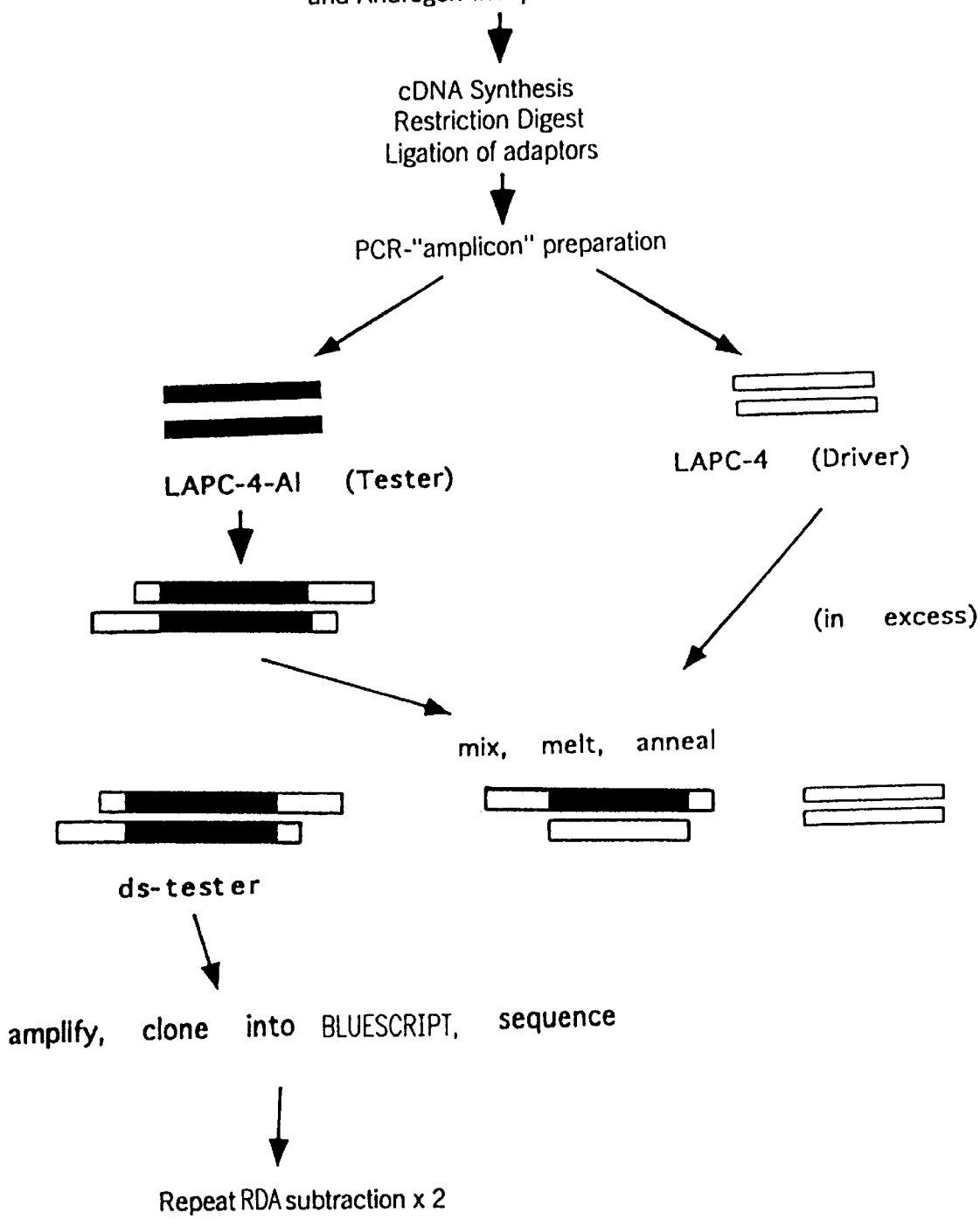
FIG. 6 is a flow chart showing the scheme of representational difference analysis (RDA).
Figure 7:
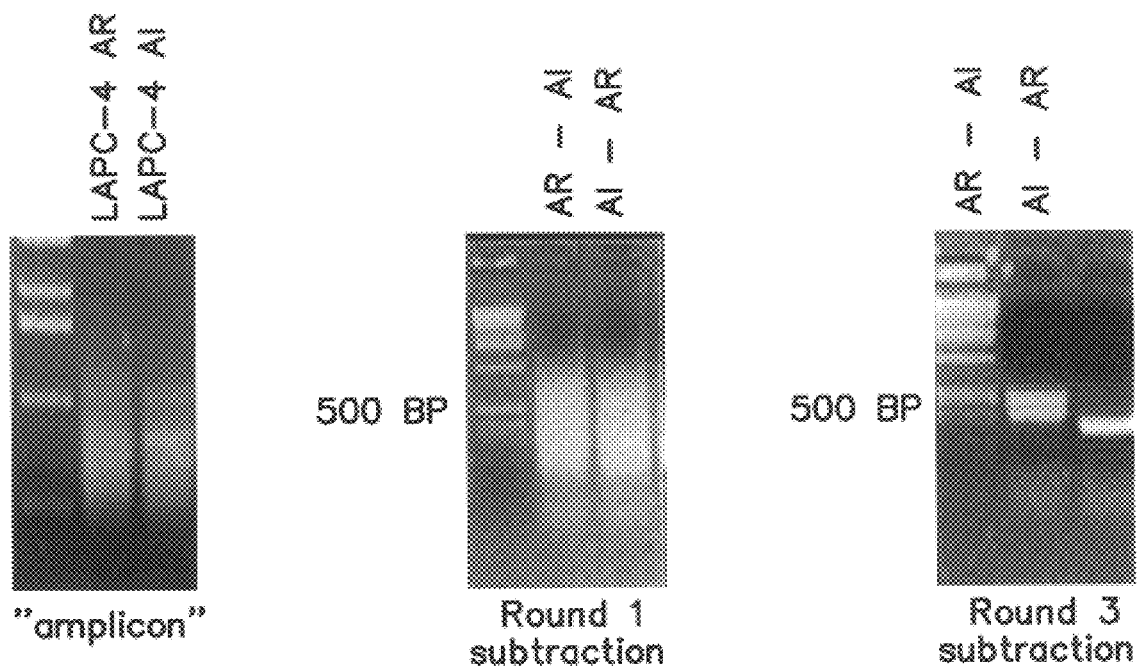
FIG. 7 shows the results of representational difference analysis (RDA) of LAPC-4 androgen responsive (AR) and LAPC-4 androgen independent (AI) cells after 1 and 3 rounds of subtraction.

Subtractions are performed in both directions, one direction serving as a control for the other. cDNAs present in both populations will form heterodimers, whereas uniquely expressed cDNAs will form homodimers. These uniquely expressed cDNAs can be amplified, then used for a second round of subtraction. An example of this technique is shown in FIG. 6. After 2–3 rounds of subtraction, unique bands appear in each direction. The results after 1 and 3 rounds of subtraction using LAPC-4 AR and AI are shown in FIG. 7. These can then be isolated, subcloned, and sequenced. Table 4 is a partial summary of differentially expressed genes that have been identified to date.

Table 4. Partial summary of genes identified by RDA, grouped into those whose differential expression has been confirmed, those likely to represent membrane proteins, and unknown or non-membrane proteins RDA Clones Confirmed to be Differentially Expressed in LAPC-4 Androgen Independent Tumor
human DNAj
renal kallikrein
gbH38038—murine E25 homologue
nm23 H2
clone 29 (no match)
RDA Clones
novel G protein coupled receptor kinase
(adrenergic receptor homologue)
laminin homologue
CD9
corticosteroid binding globulin (poor match)
Other RDA Clones
7 EST matches
ornithine decarboxylase
glutathione peroxidase
4 ribosomal gene
N acetyl transferase homologue
HSP 70 cognate Differential Expression of Genes by RDA in Prostate Cancer Cell Lines and Xenografts Thus far, more than thirty genes have been identified by RDA (Table 4). Based on sequence analysis, criteria have been established for prioritizing the order in which RDA clones are analyzed. Sequences are initially analyzed using BLAST searches of widely available databases such as GenBank. Because RDA clones which encode cell surface or secreted proteins are likely to be of functional and diagnostic importance, clones with these features first were analyzed first. Second priority was given in the analysis to clones without recognizable motifs which have no databank matches.

Figure 8A:
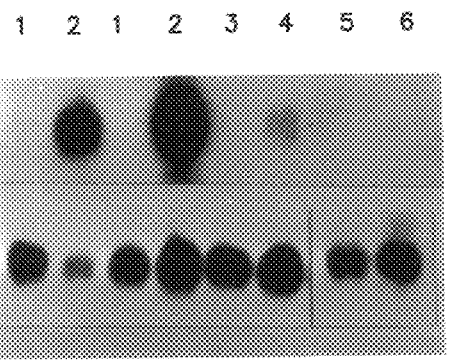
FIGS. 8(A–B) shows the results of a northern blot (8A) and S1 nuclease protection (8B) for E25a RNA in androgen responsive and androgen independent cells.
Figure 8B:
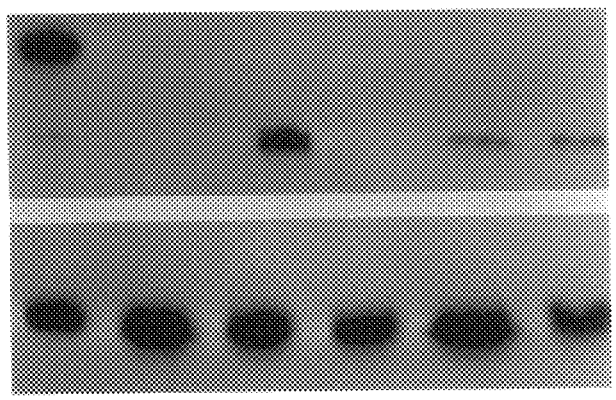
Figure 9:
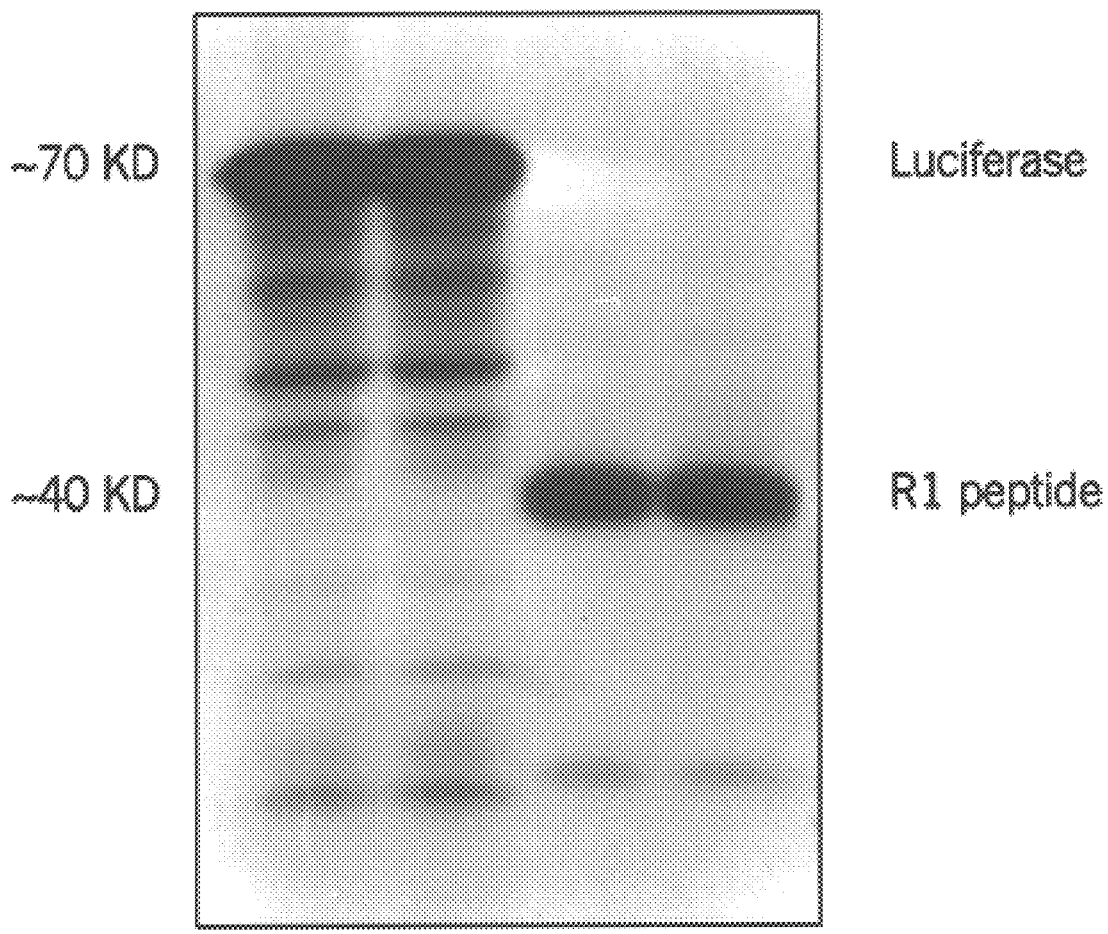

E25 protein is a novel type II integral membrane protein obtained by 5' and 3' RACE extension of an RDA clone selected for analysis because it encodes a large hydrophobic region suggestive of a transmembrane protein. It is 80% homologous to murine E25, a marker of osteogenic differentiation. Northern blot and S1 nuclease analyses confirm that E25a protein is differentially expressed in the androgen independent LAPC-4 xenograft and an androgen independent LNCaP subline, further strengthening the association of this gene with androgen independence (Thalmann et al., 1994) (FIG. 8). E25a protein is not detectably expressed in normal prostate tissue at the sensitivity of an RNA blot (FIG. 8A, lane 6), but is expressed in BPH tissue from a patient with basal cell hyperplasia (FIG. 8B, lane 7). This result suggests that E25a protein is selectively expressed in basal cells and in androgen independent prostate cancer. In vitro transcription-translation demonstrates that the E25a nucleic acid molecule encodes a 40 kd protein (FIG. 9).

Antiserum directed against an E25a GST-fusion protein has been generated and polyclonal antibodies directed against the extracellular domain and against the intracellular domain of E25a protein have been identified.

Prostate cancer has a unique propensity to metastasize to bone, where it forms blastic lesions. E25a protein, therefore, might serve as an adhesion molecule and mediate attachment to bone. Alternatively, it might be involved in inducing new bone formation by prostate metastases.

EXAMPLE 3

Isolation of Additional Candidate Genes Encoding Molecules which are Structurally and/or Functionally Related to E25a Protein In order to expand the number of clones generated by RDA, one can modify the initial protocol in five respects. First, one can use additional four base cutters (i.e., Tsp5O9) in order to expand the number of genes represented in the "driver" and "tester" populations. Second, one can synthesize cDNA using both random hexamers and oligodT primers, since with random hexamers one may obtain more 5' sequence from larger genes. Third, in the initial experiments, the majority of RDA fragments were less than 500 bp, most likely the result of PCR bias. By size selecting the "driver" population up front, one can generate larger products and expand the number of isolated genes. Fourth, one can analyze clones after one and two rounds of subtraction instead of three. As will be described below, this would increase the number of clones obtained. Finally, and most importantly, one can apply RDA to new androgen dependent and independent xenograft tumors.

Two RDA experiments can be performed in parallel. LAPC-4 cDNA can be used as "tester" in order to isolate cell surface molecules upregulated in androgen responsive prostate cancer. cDNA from the androgen independent xenograft can be used as a "tester" in order to identify molecules upregulated in androgen independent prostate cancer.

RDA clones can be arrayed in 96 well plates and tested for differential expression by a "reverse" northern analysis.

In the initial RDA experiments, cDNAs were subjected to three rounds of subtraction in order to obtain a relatively "pure" population of highly differentially expressed genes. These genes were sequenced, and clones with cell surface motifs or novel sequence were chosen for analysis. In order to increase the yield from RDA and isolate genes differentially expressed to a smaller degree (i.e., 5:1 instead of 100:1), one can perform fewer rounds of subtraction and screen resulting clones for differential expression. A high throughput "reverse northern" analysis can be used to screen genes for differential expression rapidly. In this assay, RDA products are arrayed in a 96 well grid and transferred to nitrocellulose. The blot is then probed with labeled androgen dependent and independent "driver" cDNA. Preliminary data comparing standard northern analysis with "reverse" analysis have confirmed the differential expression of RDA products tested.

EXAMPLE 4

Analysis of Expression of Isolated Gene Products in Normal Prostate and in Androgen Dependent and Androgen Independent Prostate Cancer Patient Samples In situ hybridization to determine the expression profiles of E25a and other candidate genes Prostate cancer samples are extremely heterogeneous and are typically comprised of a mixture of normal and hyperplastic glands, as well as both well- and poorly-differentiated cancers. To evaluate the expression of candidate genes accurately, it is important to examine their expression on a cell-by-cell basis. Immunohistochemical analysis can be performed when antibodies are available. In the absence of antibody reagents, one can use in situ hybridization (ISH).

Recombinant plasmid pCRII (Invitroge, San Diego, Calif.) containing the full-length human E25a gene, was linearized to generate antisense and sense digoxigenin-labeled riboprobes. In situ hybridization was performed on an automated instrument (Ventana Gen II, Ventana Medical Systems) as previously described (Loda, M. et al., 1996, Expression of mitogen-activated protein kinase phosphatase-1 in the early phases of human epithelial carcinogenesis, American Journal of Pathology 149:1553–1564).

Figure 10A:
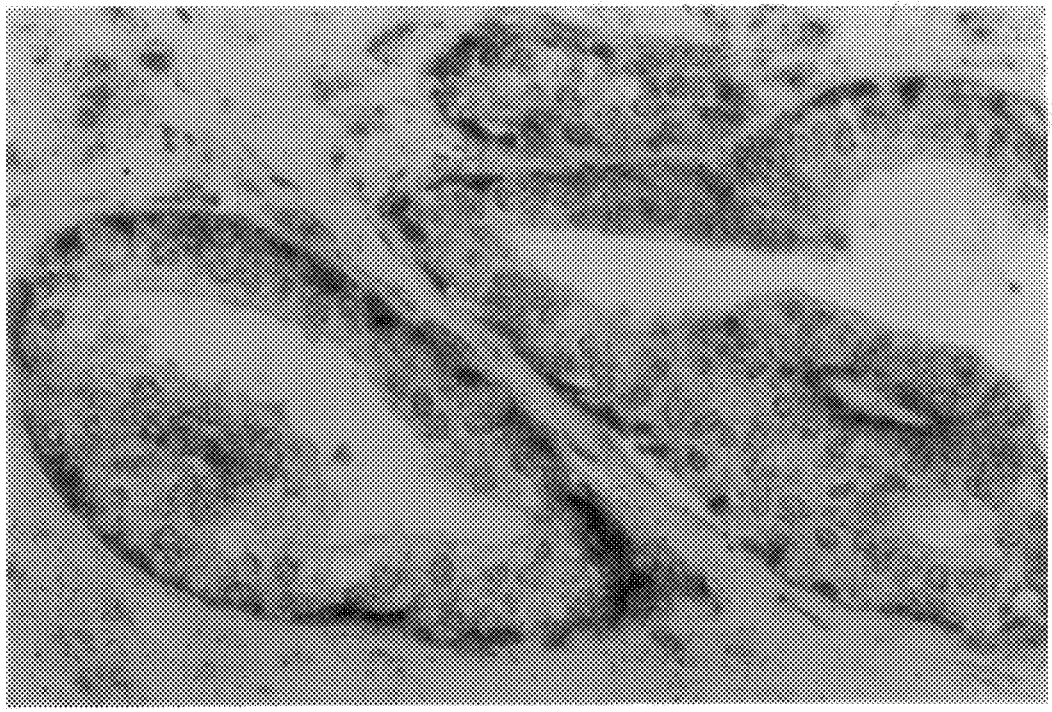
FIG. 10A shows a tissue section from normal prostate showing in situ hybridization of an E25 probe. The probe specifically labels basal cells.
Figure 10B:
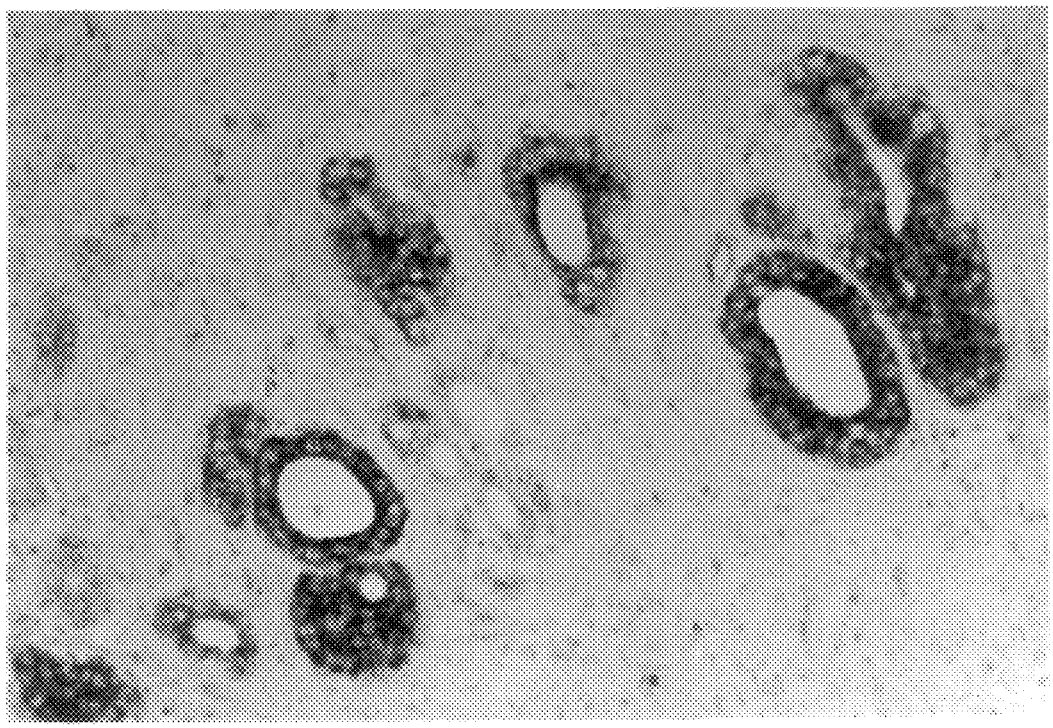
FIG. 10B shows a tissue section from an androgen independent prostate tumor showing strong labelling by in situ hybridization of an E25 probe.

E25a RNA expression in normal prostate tissue is localized to the basal epithelium (FIG. 10A). E25a RNA is expressed in tissue samples from prostate cancer of all stages, including androgen independent tumors (FIG. 10B).

Tissue samples from radical prostatectomies were analyzed by ISH. The results are summarized in Table 5.

TABLE 5

In situ hybridization for E25a in radical prostatectomy samples

| Cell Type | Proportion of Cells Positive for E25a |
|---|---|
| Basal cells | 12 of 12 |
| Secretory cells | 1 of 20 |
| Prostatic intraepithelial neoplasia (PIN) | 8 of 8 |
| Invasive cells | 18 of 20 |

In addition, E25a-positive lymphocytes were found in three cases. These lymphocytes were infiltrating, and therefore most likely activated lymphocytes.

In colon, E25a RNA is not expressed in normal samples, but is expressed in 4 of the 4 specimens of colon cancer tested. Similar results were obtained from samples of breast tissue, wherein cancerous tissue was positive for E25a and normal tissue was negative.

These results suggest that in situ hybridization to detect E25a RNA is useful for distinguishing normal androgen dependent prostate tissue from cancerous prostate tissue and androgen independent prostate tissue (basal cells). For non-prostatic tissue, E25a in situ hybridization can be used to distinguish cancerous from normal tissue. This method is particularly suited for detection of carcinoma.

Expression profiles of candidate genes can be generated by screening the following tissues: normal prostate; well-differentiated prostate cancer (before and after hormone therapy); poorly differentiated prostate cancer; hormone refractory prostate cancer (localized and metastatic). Non-prostate tissue can be used. Between two and five specimens from each category may be analyzed.

Northern Analysis of E25a Expression in Multiple Tissues

Figure 11:
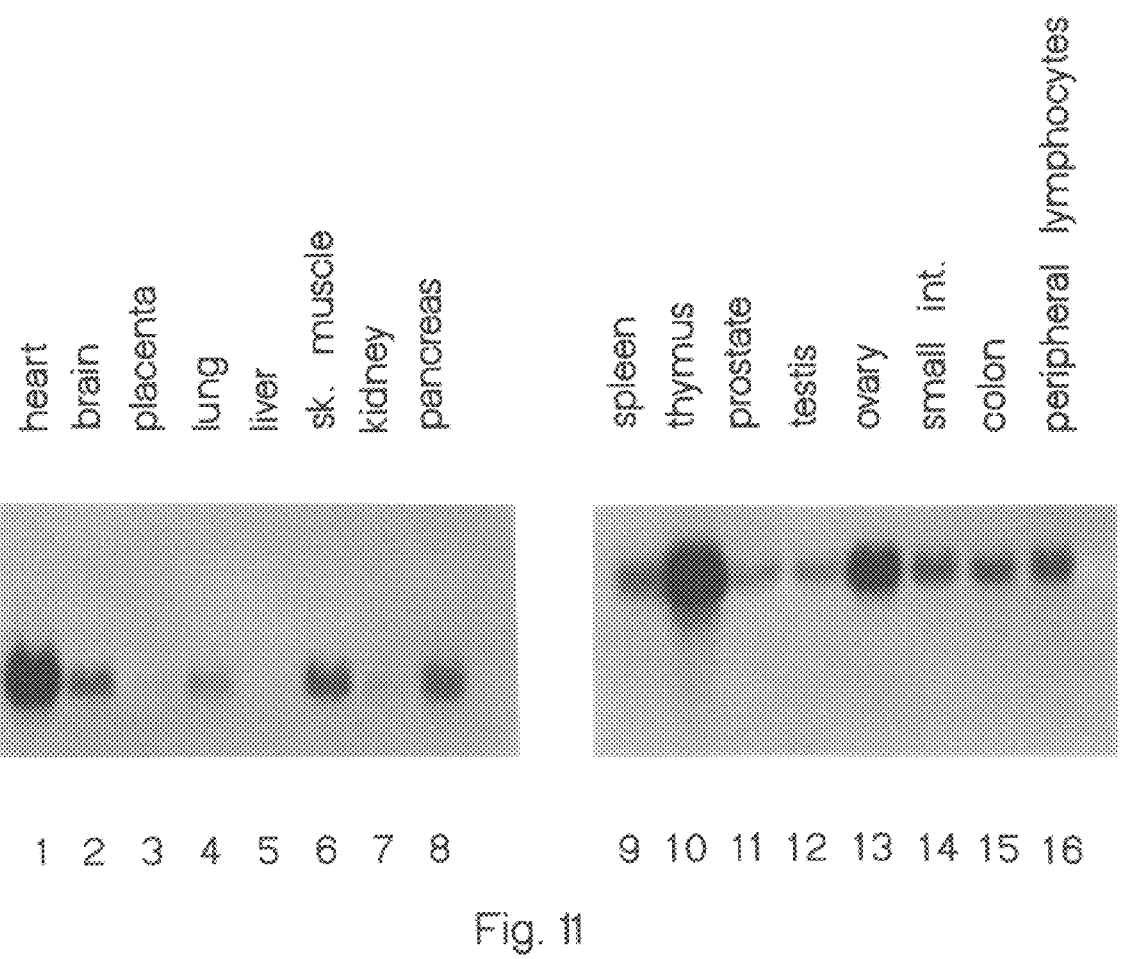
FIG. 11 shows an autoradiogram from a northern blot analysis of E25 expression in multiple tissues. Lanes 1–16 represent samples from heart, brain, placenta, lung, liver, skeletal muscle, kidney, pancreas, spleen, thymus, prostate, testis, ovary, small intestine, colon and peripheral lymphocytes, respectively.

Expression of an E25a nucleic acid molecule was analyzed in samples from heart, brain, placenta, lung, liver, skeletal muscle, kidney, pancreas, spleen, thymus, prostate, testis, ovary, small intestine, colon and peripheral lymphocytes by northern blotting using a commercial preparation (Clontech) with 2 ng polyA selected RNA per lane (equivalent to 200 ng total RNA). The results are shown in FIG. 11. The level of E25a nucleic acid molecule expression in thymus was compared to that in LAPC-4 androgen independent cells. LAPC-4 cells expressed 1.5 to 2 times as much of the E25a nucleic acid molecule as thymus.

Cloning of Full-length cDNAs and Preparation of Antibodies for Genes Selected for Biological Characterization The following criteria can be used to select genes for biological characterization: 1) genes expressed only in androgen independent cancers; 2) genes differentially expressed pre- and post-hormonal therapy; 3) genes expressed in basal cells and androgen independent cancers; 4) genes whose expression correlates with tumor grade. Full-length clones can be obtained by screening an already constructed LAPC-4 androgen independent cDNA library, or alternatively using 5' and 3' RACE-PCR, as was done for the human E25a homologue. In parallel with the cloning of full length cDNAs, GST-fusion proteins can be generated for the production of polyclonal antibodies. Antibodies can be affinity purified and used for biological studies.

Polyclonal antibody against intracellular portion of E25a protein was produced by immunizing rabbits with a GST-fusion protein encoding only the amino terminal portion of E25a protein. Antibodies to the extracellular portion of E25a protein were produced by immunizing with a GST-fusion containing the carboxyl terminus of E25a protein.

EXAMPLE 5
Testing the Biological Effects of Candidate Genes on Androgen Independent Growth in Vivo Some genes upregulated in hormone refractory prostate cancer may contribute to the pathogenesis of androgen independence. Bcl-2, for example, which is upregulated in many advanced prostate cancers, has been demonstrated to confer androgen independence to the androgen dependent LNCaP prostate cancer cell line (Raffo et al., 1995). In accordance with this example, one can assess in vivo the contribution of candidate genes to the androgen independent phenotype.

LAPC-4 Androgen Dependent Tumor Explants Grow in Tissue Culture and Form Androgen Dependent Tumors upon Reinjection into SCID Mice Current bioassays for androgen dependent and independent growth rely almost exclusively on the LNCaP prostate cancer cell line, because it is the only cell line available which displays features of androgen dependence. In order to circumvent the problem of long-term passaged cell lines with the potential for multiple in vitro mutations, the LAPC-4 xenograft was grown in short term culture and then reinjected into mice to form tumors. Explanted tumors were then be manipulated genetically and the effects of these manipulations was measured in vivo.

LAPC-4 tumors were minced into small pieces and cultured in media with 15% fetal calf serum. Outgrowth of both epithelial cells and fibroblasts was noted after 2–3 days. Cells then grew to confluence and could be successfully passaged to remove the original tumor pieces. RT-PCR confirmed continued PSA expression. 1×10$^7$ cells were then reinjected into either intact male or castrated SCID mice. Similar to the initial experiments, injected cells formed tumors in an androgen dependent fashion, requiring prolonged periods to form tumors in castrated mice.

LAPC-4 Cultures can be Transduced with Retrovirus

In order to test the infectability of explanted LAPC-4 cells by retrovirus, these cells were transduced with a retroviral vector containing a truncated nerve growth factor receptor gene (NGFR). A PG13 packaging cell line, containing the gibbon-ape leukemia virus (GALV) envelope, was used to generate high titer virus. Retrovirus virions produced in this manner have the unique property of infecting human, but not murine, cells, thus avoiding introduction of transgene into mouse stromal cells (Bauer et al., 1995). After infection, the cells were stained with an antibody directed against NGFR and analyzed by FACS analysis. Five-10% of cells were transduced. Murine fibroblast negative controls showed no infection, while human 293T cells were efficiently transduced.

Biological Assays for cDNAs Upregulated in Androgren-independent Prostate Cancer Candidate cDNAs can be cloned into the 5' position of the retroviral vector pSRalpha used extensively in our laboratory (Afar et al., 1994). A reporter gene, either NGFR, LacZ, or human codon-optimized green fluorescent protein (GFP), would be inserted downstream. The plasmid can be transfected into the PG13 packaging cell line, virus collected, and titers measured. LAPC-4 cells can be infected after the first passage and then expanded without selection until sufficient numbers are available for injection. Transgene expression can be confirmed either by FACS analysis or by northern blot analysis using the RDA cDNA clone as a probe.

Two different types of experiments can be performed. In the first, infected cells are injected into the flanks of intact male SCID mice. After tumors form in both flanks of an individual mouse, one tumor is removed and the mouse is then castrated. The explanted tumor is analyzed to quantify the percentage of cells infected. This can be done either by LacZ staining or by FACS analysis for GFP or NGFR. We anticipate that 5–10% of cells will carry the transgene. The remaining tumor can be similarly analyzed after it regresses and regrows (i.e., about 4–8 weeks after castration). If the transgene confers a survival advantage or androgen independence to infected cells, we would expect to see the percentage of cells carrying the transgene to increase after hormone ablation. Multiple mice can be injected with each construct and positive results confirmed by repetition.

In a second set of experiments, one can implant infected cells into intact and castrated male mice in parallel after quantifying infection frequency. Resulting tumors (at 4 and 12 weeks, respectively) are analyzed for insert frequency as described above. Again, we expect that "androgen independent" genes will provide an androgen independent growth advantage and predominate in the resulting tumor. In addition, it is possible that a given candidate gene will shorten the time to tumor formation in castrated males. This can also be measured. Finally, it is possible that a given gene could cause aggressive androgen dependent growth. This too can be quantified in this assay, by comparing time to tumor formation and insert frequency before and after injection into intact male mice.

These assays can be validated with positive controls. In particular, one can use bcl-2, c-myc, and c-met, since these have been consistently associated with androgen independence.

EXAMPLE 6
Growth in Soft Agar as an Alternative Assay for Androgen Independence

LNCaP is an androgen dependent prostate cell line derived from a lymph node metastasis. LNCaP cells grow poorly in androgen depleted medium and do not form tumors in castrated mice. LNCaP also does not grow in soft agar (Wu et al., 1994). Raffo and colleagues introduced the bcl-2 oncogene into LNCaP and demonstrated that bcl-2 overexpression could confer androgen independence, as measured by the ability of transfected LNCaP to grow in androgen depleted medium and form tumors in castrate mice (Raffo et al., 1995). Bcl-2 transfected cells also gained the ability to grow in soft agar, a possible alternative marker of androgen independence.

Figure 12:
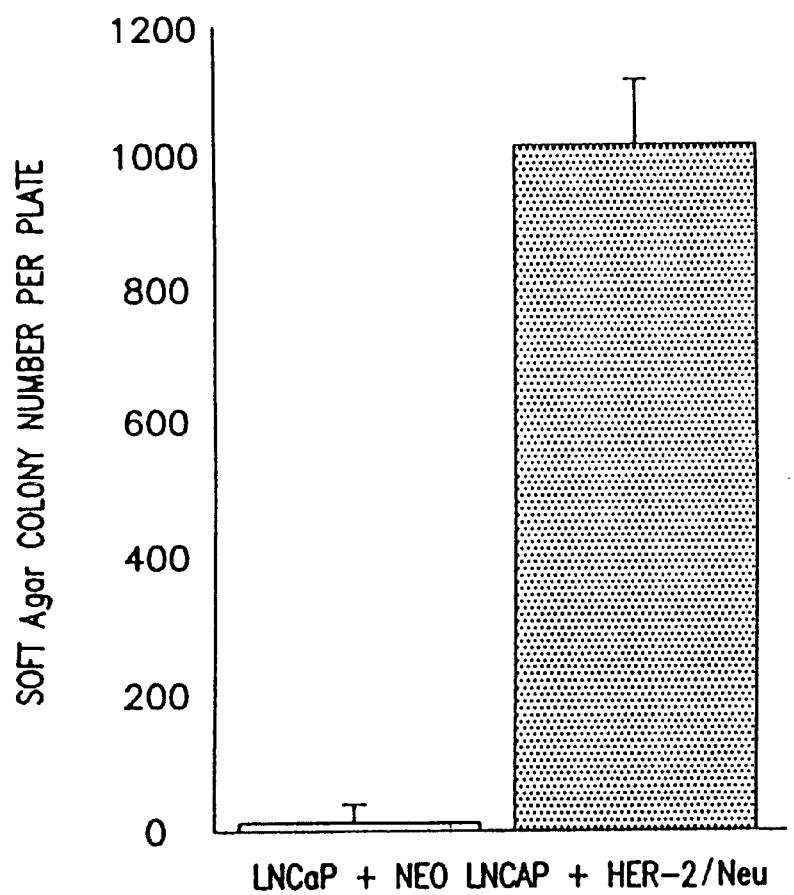
FIG. 12 shows expression of Her-2/Neu in LNCaP cells resulting in growth in soft agar. The number of colonies greater than 0.5 mm in size was scored after 2 weeks.

The growth of LNCaP has been altered by introduction of a single gene. The Her-2/neu tyrosine kinase receptor is overexpressed in human breast and ovarian cancer and may play a role in a subset of prostate cancers (Kuhn et al., 1993; Sadasvian et al., 1993; Slamon et al., 1989). LNCaP cells express low levels of Her-2/neu. Retroviral gene transfer was used to introduce Her-2/neu into LNCaP cells and the cells were plated in soft agar. The results show dramatic conversion to anchorage-independent growth (see FIG. 12).

Thus, LNCaP cells can be efficiently infected by retrovirus. In addition, introduction of a single gene can confer anchorage-independent growth (i.e., Her-2/neu and bcl-2) or androgen independent growth (i.e., bcl-2) to LNCaP cells.

EXAMPLE 7

Androgen Independence Conferred on LNCaP Cells Infected with an E25a Nucleic Acid Molecule LNCaP is an androgen dependent prostate cell line derived from a lymph node that does not express E25a (FIG. 8B). In this example, the ability of E25a to influence LNCaP tumor growth in vivo was tested by implanting LNCaP cells tranfected with the E25a gene into SCID mice and measuring tumor growth.

Figure 13:
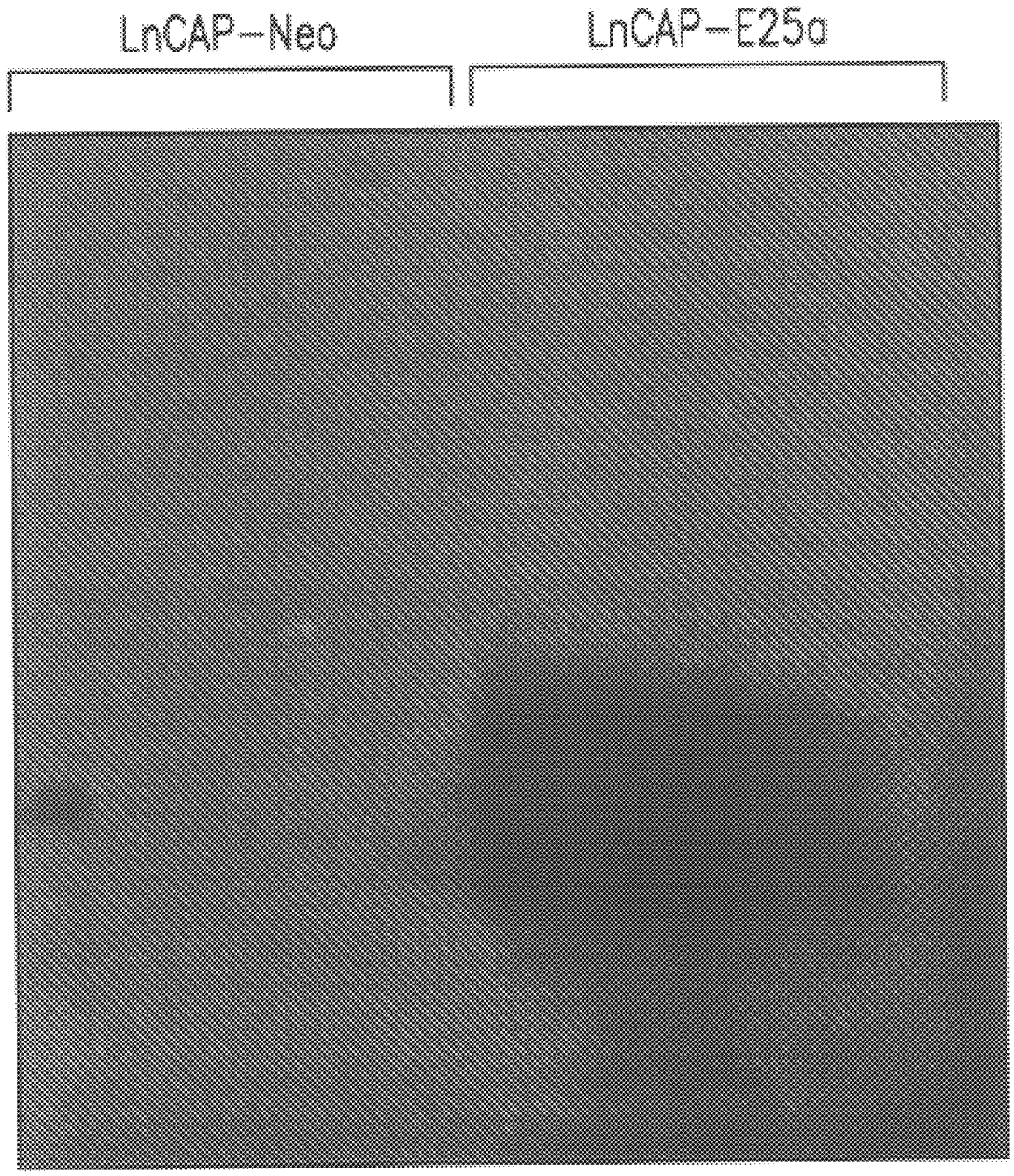
FIG. 13 shows an autoradiogram from a western blot using an E25 polyclonal antibody comparing E25 expression in LNCaP cells infected with DNA encoding E25a (LnCAP-AIX18) and with a neomycin resistance gene (LnCAP-Neo).

E25a gene was cloned into the retroviral vector PSR alpha. This vector was then cotransfected together with amphotropic packaging vector into 293T cells and amphotropic retrovirus collected from the medium at set time points. This virus was then used to infect LnCAP cells. Control virus contained neomycin resistance gene alone. The infected experimental cells were designated LNCaP-E25 and the infected control cells LNCaP-neo. For protocol, see Afar D. E., et al., 1994, Differential complementation of Bcr-Abl point mutants with c-myc, Science 264:424–426. Western blotting using an E25a polyclonal antibody confirmed expression of an E25a nucleic acid molecule by LNCaP-E25 cells (FIG. 13).

$2 \times 10^6$ LNCaP-E25 or LNCaP-neo cells were implanted subcutaneously into castrated SCID mice. Tumors were measured at days 38, 45, 59, 59 and 87 using calipers. Two independent experiments were conducted, with a total (combined across experiments) of 20 subjects in each group.

Figure 14:
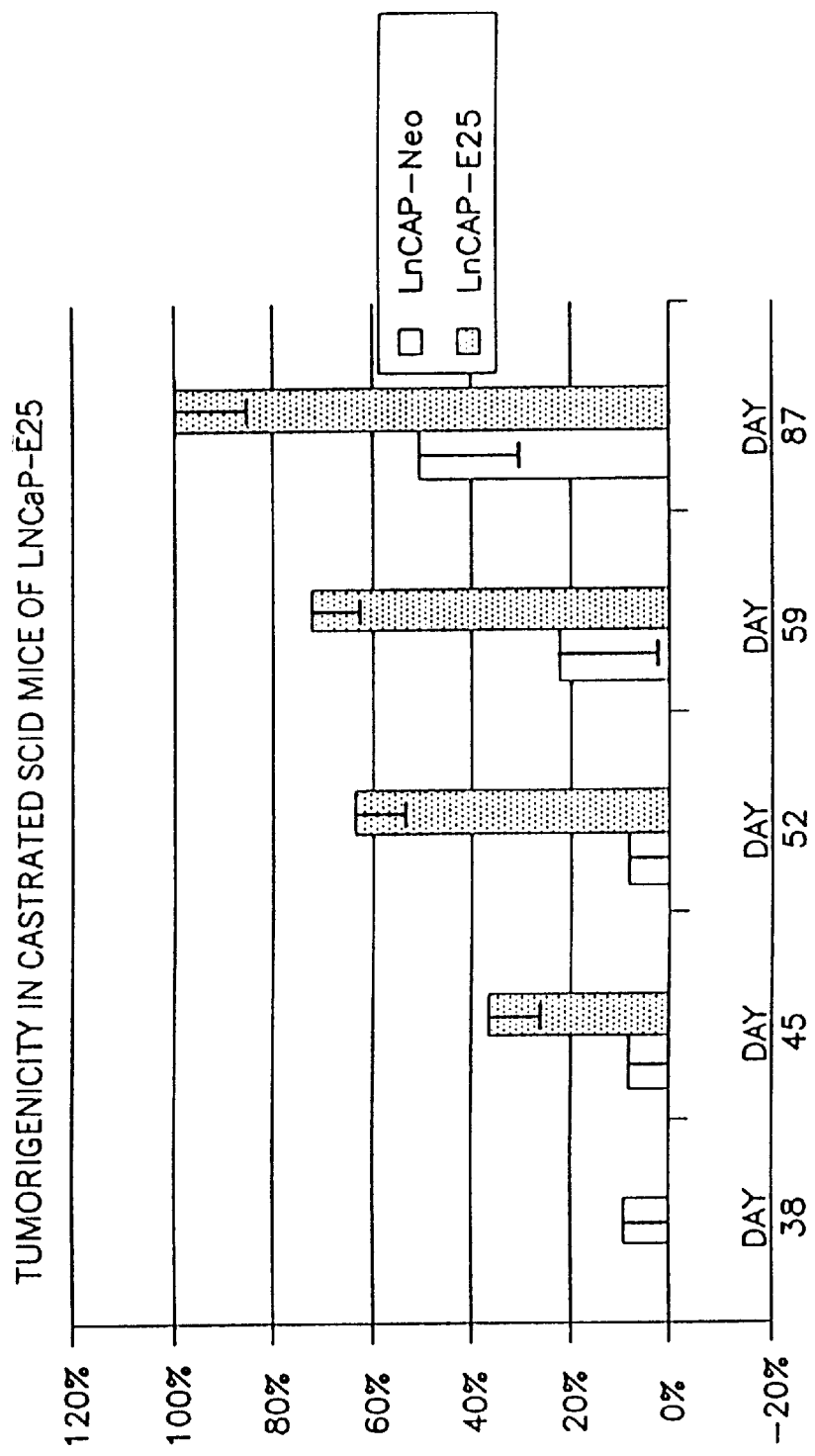
FIG. 14 shows tumorigenicity in castrated SCID mice of subcutaneously implanted LNCaP cells infected with DNA encoding E25a (LnCAP-E25) or with a neomycin resistance gene (LnCAP-Neo).

As shown in FIG. 14, LNCaP-E25 grafts formed tumors sooner and more frequently than control grafts. The average tumor size for LNCaP-E25 grafts was more than 10-fold greater than for LNCaP-neo grafts (FIG. 15). These data show that expression of an E25a nucleic acid molecule can influence tumor growth and androgen independence in vivo and suggest that molecules targeted to E25a molecules can be useful for inhibition of tumor cell proliferation and treatment of cancer such as hormone refractory prostate cancer.

REFERENCES

Afar, D. E., Goga, A., McLaughlin, O. N., Witte, O. N., and Sawyers, C. L. (1994). Differential complementation of Bcr-Abl point mutants with c-myc. Science 264,424–426.

Aldrovandi, G. M., Feuer, G., Gao, L., Jamieson, B., Kristeva, M., et al. The SCID-hu mouse as a model for HIV-1 infection. Nature 363, 732–736 (1993).

Bauer, T. R., Miller, A. D., and Hickstein, D. D. (1995). Improved transfer of the leukocyte integrin CD18 subunit into hematopoietic cell lines by using retroviral vectors having a gibbon-ape leukemia virus envelope. Blood 86, 2379–2387.

Bonkhoff, H., and Remberger, K. (1996). Differentiation pathways and histogenetic aspects of normal and abnormal prostatic growth: a stem cell model. The Prostate 28, 98–106.

Bonkhoff, H., Stein, U., and Remberger, K. (1994). The proliferative function of basal cells in the normal and hyperplastic human prostate. The Prostate 24, 114–118.

Bookstein, R., MacGrogan, D., Hilsenbeck, S. G., Sharkey, F., and Allred, D. C. (1993). p53 is mutated in a subset of advanced-stage prostate cancers. Cancer Research 53, 3369–3373.

Brass, A., Barnard, J., Patai, B. L., Salvi, D., and Rukstalis, D. B. (1995). Androgen up-regulates epidermal growth factor receptor expression and binding affinity in PC3 cell lines expressing the human androgen receptor. Cancer Research 55, 3197–3203.

Braun, B. S., Frieden, R., Lessnick, S. L., May, W. A., and Denny, C. T. (1995). Identification of target genes to the Ewing's sarcoma EWS/FLI fusion protein by representational difference analysis. Molecular Cellular Biology In Press.

Brothman, A. R., Peehl, D. M., Patel, A. M. and McNeal, J. E. Frequency and Pattern of Karyotypic Abnormalities in Human Prostate Cancer. Canc. Res. 50, 3795–3803 (1990).

Coutant, K. D., Corvaia, N., and Ryder, N. S. (1995). Bradykinin induces tyrosine phosphorylation of epidermal growth factor receptor and focal adhesion proteins in human keratinocytes. Biochemical Biophysics Research Communications 2105, 774–780.

Crowley, C. W., Cohen, R. L., Lucas, B. K., Liu, G., Shuman, M. A., and Levinson, A. D. (1993). Prevention of metastasis by inhibition of the urokinase receptor. Proceedings of the National Academy of Sciences 90, 5021–5025.

Culig, Z., Hobisch, A., Cronauer, M. V., Radmayr, C., Trapman, J., Hittmair, A., Bartsch, G., and Kocker, H. (1994). Androgen receptor activation in prostatic tumor cell lines by insulin-like growth factor-1, keratinocyte growth factor, and epidermal growth factor. Cancer Research 54, 5474–5478.

Debruyne, F. M., Collins, V. P., van Dekken, H., Jenkins, R. B., Kocker, H., et al. Cytogenetics of prostate cancer. Consensus Conference on Diagnosis and Prognostic Parameters in Localized Prostate Cancer. Scand J Urol Neph 162, 65–71, 115–27 (1993).

Dong, J. T., Lamb, P. W., Rinker-Schaeffer, C. W., Vukanovic, J., Ichikawa, T., Isaacs, J. T., and Barrett, J.C. (1995). KAI 1, a metastasis suppressor gene for prostate cancer on human chromosome 11p11.2. Science 268, 884–886.

Ewing, C. M., Ru, N., Morton, R. A., Robinson, J. C., Wheelock, M. J., Johnson, K. R., Barrett, J. C., and Isaacs, W. B. (1995). Chromosome 5 suppresses tumorigenicity of PC3 prostate cancer cells: correlation with re-expression of alpha-catenin and restoration of E-cadherin function. Cancer Research 55, 4813–4817.

Gaylis, F. D., Keer, H. N., Wilson, M. J., Kwaan, A. A., Sinha, A. A., and Kozlowski, J. M. (1989) Plasminogen activators in human prostate cancer cell lines and tumors: correlation with the aggressive phenotype. Journal of Urology 142, 193–198.

Ghossein, R. A., Scher, H. I., Gerald, W. L., Kelley, W. K. Curley, T., et al. Detection of circulating tumor cells in patients with localized and metastatic prostatic carcinoma: Clinical implications. J. Clin. Onc. 13, 1195–1200 (1995).

Gleave, M. E., Hsieh, J. T., Wu, H. C., von Eschenbach, A. C. and Chung, L. W. K. Serum prostate specific antigen levels in mice bearing human prostate LNCaP tumors are determined by tumor volume and endocrine and growth factors. Canc.Res. 52, 1598–1605 (1992).

Hermann, A., Buchinger, P., and Rehbock, J. (1995). Visualization of tissue kallikrein in human breast carcinoma by two-dimensional western blotting and immunohistochemistry. Biological Chemistry Hoppe Seyler 376, 365–370.

Hobisch, A., Culig, Z., Radmayr, C., Bartsch, G., Klocker, H., and Hittmair, A. (1995). Distant metastases from prostatic carcinoma express androgen receptor protein. Cancer Research 55, 3068–3072.

Horoszewicz, J. S., Leong, S. S., Kawinski, E., Karr, J. P., Rosenthal, H., et al. LNCaP model of human prostate carcinoma. Canc.Res. 43, 1809–1818 (1983).

Hsu, S. M., Raine L. and Fanger, H. A. comparative study of the peroxidase-antiperoxidase method and an avidin-biotin complex method for studying polypeptide hormones with radioimmunoassay antibodies. Am T Clin Path 75, 734–738 (1981).

Katz, A. E., Olsson, C. A., Raffo, A. J., Cama, C., Perlman, H., et al. Molecular staging of prostate cancer with the use of an enhanced reverse transcriptase-PCR assay. Urology 43, 765–775 (1994). Kleinerman, D. I., Zhang, W. W., Lin, S. H., Nguyen, T. V., von Eschenbach, A. C., and Hsieh, J. T. (1995). Application of a tumor suppressor (C-CAM I) expressing recombinant adenovirus in androgen independent human prostate cancer therapy: a preclinical study. Cancer Research 55, 2831–2836.

Kokontis, J., Takakura, K., Hay, N., and Liao, S. (1994) Increased androgen receptor activity and altered c-myc expression in prostate cancer cells after long-term androgen deprivation. Cancer Research 54, 1566–1573.

Koshikawa, N., Yasumitsu, H., Umeda, M., and Miyazaki, K. (1992). Multiple secretion of matrix serine proteinases by human gastric carcinoma cell lines. Cancer Research 52, 5046–5053.

Krongrad, A., Allman, D. R., Brothman, A. R., and McPhaul, M. J. (1991). The expression of human androgen receptor in an unresponsive human prostate cancer cell line is insufficient to confer androgen responsiveness. Journal of Urology 145, Abstract 331.

Krongrad, A., and Bai, G. (1994). C-fos promoter insensitivity to phorbol ester and possible role of protein kinase c in androgen independent cancer cells. Cancer Research 54, 6073–6077.

Kuhn, E. J., Kurnot, R. A., Sesterhenn, 1. A., Chang, E. H., and Moul, J. W. (1993). Expression of the c-erb-B-2 oncoprotein in human prostatic carcinoma. Journal of Urology 150, 1427–1433.

Lim, D. J., Liu, X. L., Sutkowski, D. M., Braun, E. J., Lee, C., et al. Growth of an androgen sensitive human prostate cancer cell line, LNCaP, in nude mice. Prostate 22, 109–118 (1993).

Liu, A. Y., Corey, E., Bladou, F., Lange, P. H. and Vessella, R. L. Prostatic cell lineage market emergence of BCL2+ cells of human prostate cancer xenograft LuCaP 23 following castration. Intl J Cancer 65, 85–89 (1996).

Lisitsyn, N. A., Lisitsyn, N., and Wigier, M. (1993). Cloning of the differences between two complex genomes. Science 259, 946–951.

Lokeshwar, B. L., Selzer, M. G., Block, N. L., and Gunja-Smith, Z. (1993). Secretion of matric metalloproteinases and their inhibitors by human prostate in explant cultures: reduced tissue inhibitor of metalloproteinase secretion by malignant tissues. Cancer Research 53, 4493–4498.

McDonnell, T. J., Troncoso, P., and Brisbay, S. M. (1992). Expression of the protooncogene bcl-2 in the prostate and its association with emergence of androgen independent prostate cancer. Cancer Research 52, 6940–6944.

McKeehan, W. L. (1991). Growth factor receptors and prostate cell growth. In Prostate cancer: cell and molecular mechanisms in diagnosis and treatment. J. T. Isaacs, ed. (New York: Cold Spring Harbor Laboratory Press), pp. 165–173.

Micale, M. A., Sanford, J. S., Powell, I. J., Sakr, W. A. and Wolman, S. R. Defining the extend and nature of cytogenetic events in prostatic adenocarcinoma: paraffin FISH vs. metaphase analysis. Cancer Gen Cytogen 69, 7–12 (1993).

Pajouh, M. S., Nagle, R. B., Breathnach, J. S., Finch, J. S., Brawer, M. K., and Bowden, G. T. (1991). Expression of metalloproteinase genes in human prostate cancer. Journal of Cancer Research Clinical Oncology 117, 144–50.

Pang, S., Taneja, S., Dardashti, K., Cohan, P., Kaboo, R., et al. Prostate tissue specificity of the prostate-specific antigen promoter isolated from a patient with prostate cancer. Human Gene Ther. 6, 1417–1426 (1995).

Pisters, L. L., Troncoso, P., Zhau, H. E., Li, W., von Eschenbach, A. C., and Chung, L. (1995). c-met protooncogene expression in benign and malignant human prostate tissues. Journal of Urology 154,293–298.

Pretlow, T. G., Delmoro, C. M., Dilley, G. G., Spadafora, C. G. and Pretlow, T. P. Transplantation of Human Prostatic Carcinoma into Nude Mice in Matrigel, Canc. Res. 51, 3814–3817 (1991).

Raffo, A. J., Perlman, H., Chen, M.-W., Day, M. L., Streitman, J. S., and Buttyan, R. (1995). Overexpression of bcl-2 protects prostate cancer cells from apoptosis in vitro and confers resistance to androgen depletion in vivo. Cancer Research 55, 4438–4445.

Rinker-Schaeffer, C. W., Partin, A. W., Isaacs, W. B., Coffey, D. S., and Isaacs, J. T. (1994). Molecular and cellular changes associated with the acquisition of metastatic ability by prostatic cancer cells. The Prostate 25, 249–265.

Ruizeveld de Winter, J. A., Janssen, P. J., Sleddens, H. M., Verieun-Mooijman, M. C., Trapman, J., Brinkmann, A. O., Santerse, A. B., Schroeder, F. H., and van der Kwast, T. H. (1994) Androgen receptor status in localized and locally progressive hormone refractory human prostate cancer. American Journal of Pathology 144, 735–746.

Sadasvian, R., Morgan, R., Jennings, S., Austenfield, M., Van Veldhuizen P., Stephens, R., and Noble, M. (1993). Overexpression of Her-2/neu may be an indicator of poor prognosis in prostate cancer. Journal of Urology 150, 126–131.

Saiki, R. K., Scharf, S., Faloona, F., Mullis, K. B., Horn, G. T., et al. Enzymatic Amplification of b-Globin Genomic Sequences and Restriction Site Analysis for Diagnosis of Sickle Cell Anemia. Science 230, 1350–1354 (1985).

Sambrook, J., Fritsch, E. F. and Maniatis, T. Molecular cloning: a laboratory manual, Cold Spring Harbor Laboratory Press: Molecular Cloning: A Laboratory Manual, 1989 Ed. 2.

Scher, H. I., and Kelly, W. K. (1993). Flutamide withdrawal syndrome: its impact on clinical trials in hormonerefractory prostate cancer. Journal of Clinical Oncology 11, 1566–1572.

Seiden, M. V., Kantoff, P. W., Krithivas, K., Propert, K., Bryant, M., et al. Detection of circulating tumor cells in men with localized prostate cancer. J. Clin. Onc. 12, 2634–2639 (1994).

Shtivelman, E. and Namikawa, R. Species-specific metastasis of human tumor cell in the severe combined immunodeficiency mouse engrafted with human tissue. PNAS 92, 4661–4665 (1995).

Slamon, D. J., Godolphin, W., Jones, L. A., Holt, J. A., Wong, S. G., Keith, D. E., Levin, W. J., Stuart, S. G., Udove, J., and Ulrich A. (1989). Studies of the Her-2/neu proto-oncogene in human breast and ovarian cancer. Science 244, 707–712.

Taplin, M.-E., Bubley, G. J., Shuster, T. D., Frantz, M. E., Spooner, A. E., Ogata, G. K., Keer, H. N., and Balk, S. P.

(1995). Mutation of the androgen receptor gene in metastatic androgen independent prostate cancer. The New England Journal of Medicine 332, 1393–1398.

Thalmann, G. N., Anezinis, P. E., Chang, S.-M., Zhau, H. E., Kim, E. E., Hopwood, V. L., Pathak, S., von Eschenbach, A. C., and Chung, W. K. (1994). Androgen independent cancer progression and bone metastasis in the LNCaP model of human prostate cancer. Cancer Research 54, 2577–2581.

Tilley, W. D., Buchanan, G., Hickey, T. E., and Bentel, J. M. (1996). Mutations in the androgen receptor gene are associated with progression of human prostate cancer to androgen independence. Clinical Cancer Research 2, 277–285.

Tilley, W. D., Wilson, C. M., Marcelli, M., and McPhaul, M. J. (1990). Androgen receptor gene expression in human prostate cancer cell lines. Cancer Research 50, 5382–5386.

Veldsholte, J., Ris-Stalpers, C., and Kuiper, G. (1990). A mutation in the ligand binding domain of the androgen receptor of human LNCaP cells affects steroid binding characteristics and response to anti-androgens. Biochemical Biophysics Research Communications 173, 534–540.

Visakorpi, T., Hyytinen, E., Koivisto, P., Tanner, M., Keinanen, R., Palmberg, C., Palotie, A., Tammela, T., Isola, J., and Kallioniemi, O. P. (1995). In vivo amplification of the androgen receptor gene and progression of human prostate cancer. Nature Genetics 9, 401–406.

Wainstein, M. A., He. F. Robinson, D. Kung, H. J., Schwarz, S., et al. CWR22: androgen dependent xenograft model derived from a primary human prostatic carcinoma. Canc. Res. 54, 6049–6052 (1994).

Wood D. P., Banks, E. R., Humphreys, S., McRoberts, J. W. and Rangnekar, V. M. Identification of bone marrow micrometastases in patients with prostate cancer. Cancer 74, 2533–2540 (1994).

Wu, H.-C., Hsieh, J.-T., Gleave, M. E., Brown, N. M., Pathak, S., and Chung, L. W. K. (1994). Derivation of androgen independent human LNCap prostatic cancer cell sublines: role of bone stromal cells. International Journal of Cancer 57, 406–412.

Yuan, S., Trachtenberg, J., Mills, G. B., Brown, T. J., Xu, F., and Keating, A. (1993). Androgen induced inhibition of cell proliferation in an androgen insensitive prostate cancer cell line (PC-3) transfected with a human androgen receptor complementary DNA. Cancer Research 53, 1304–1311.

What is claimed is:

1. An isolated protein designated E25a having the amino acid sequence shown in FIG. 1 (SEQ ID NO.2).

* * * * *